United States Patent [19]

Effland et al.

[11] Patent Number: 4,667,039
[45] Date of Patent: May 19, 1987

[54] 11-SUBSTITUTED 5H,11H-PYRROLO(2,1-C)(1,4)BENZOXAZEPINES AS ANTIPSYCHOTIC AND ANALGESIC AGENTS

[75] Inventors: Richard C. Effland, Bridgewater; Larry Davis, Sergeantsville; Kevin J. Kapples, Warren, all of N.J.

[73] Assignee: Hoechst-Roussel Pharmaceuticals Inc., Somerville, N.J.

[21] Appl. No.: 811,135

[22] Filed: Dec. 19, 1985

Related U.S. Application Data

[62] Division of Ser. No. 549,098, Nov. 7, 1983, Pat. No. 4,608,374.

[51] Int. Cl.⁴ .......................................... C07D 401/06
[52] U.S. Cl. ..................................... 546/208; 548/518
[58] Field of Search ............... 546/208; 548/524, 518

[56] References Cited

U.S. PATENT DOCUMENTS 3,558,652 12/1971 Teotino et al. ................. 514/422 X
3,629,435 1/1971 Teotino et al. ..................... 548/561

Primary Examiner—Donald G. Daus
Assistant Examiner—William A. Teoli, Jr.
Attorney, Agent, or Firm—Tatsuya Ikeda

[57] ABSTRACT

There are described to novel 11-substituted 5H,11H-pyrrolo[2,1-c][1,4]benzoxazepines of the general formula

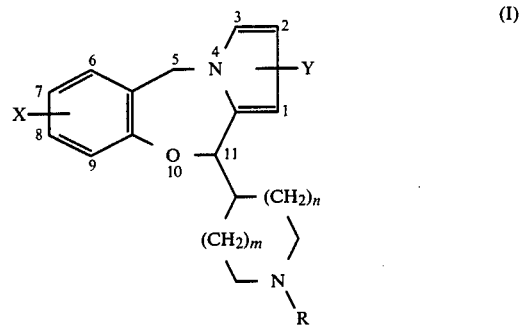

where m and n are each independently 0, 1 or 2 and m+n is 1 or 2, X and Y are each independently hydrogen, loweralkyl or halogen, and R is hydrogen, cyano, —C(NH$_2$)NOH,

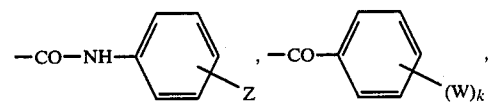

unsubstituted loweralkyl, or substituted loweralkyl having one to three substituents each of which being independently cyano, hydroxy, cyclohexyl, furyl, thienyl,

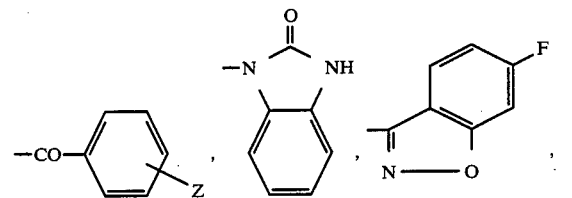

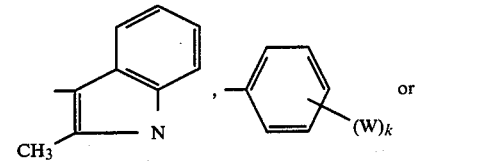

k being 1, 2 or 3, W being each independently hydrogen, halogen, hydroxy, loweralkyl, trifluoromethyl, loweralkoxy, nitro, amino, diloweralkylamino, phenoxy, or benzyloxy, and Z being hydrogen, loweralkyl or halogen, which are useful as antipsychotic and analgesic agents; novel intermediate compounds therefor; and methods of synthesizing the foregoing compounds.

10 Claims, No Drawings

11-SUBSTITUTED 5H,11H-PYRROLO(2,1-C) (1,4)BENZOXAZEPINES AS ANTIPSYCHOTIC AND ANALGESIC AGENTS

This is a division of application Ser. No. 549,098 filed Nov. 7, 1983, now U.S. Pat. No. 4,608,374.

This invention relates to novel 11-substituted 5H,11H-pyrrolo[2,1-c][1,4]benzoxazepines of the general formula

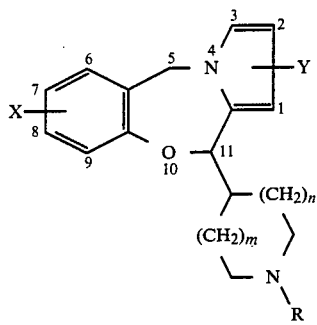

where m and n each independently 0, 1 or 2 and m+n is 1 or 2, X and Y are each independently hydrogen, loweralkyl or halogen, and R is hydrogen, cyano, —C(NH$_2$)NOH,

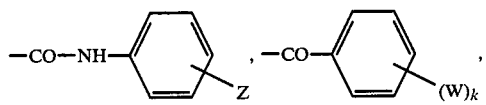

unsubstituted loweralkyl, or substituted loweralkyl having one to three substitutents each of which being independently cyano, hydroxy, cyclohexyl, furyl, thienyl,

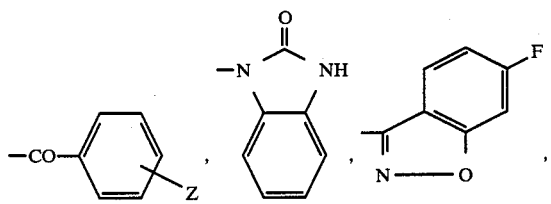

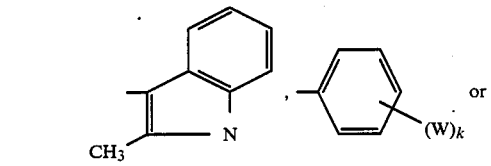

k being 1, 2 or 3, W being each independently hydrogen, halogen, hydroxy, loweralkyl, trifluoromethyl, loweralkoxy, nitro, amino, diloweralkylamino, phenoxy, or benzyloxy, and Z being hydrogen, loweralkyl or halogen, which are useful as antipsychotic and analgesic agents; to pharmaceutical compositions comprising same; to novel intermediate compounds therefor; and to methods of synthesizing the foregoing compounds.

The novel intermediate compounds of this invention mentioned above include compounds of Formula II below, where n, X and Y are as defined above and R$_s$ is methyl or benzyl.

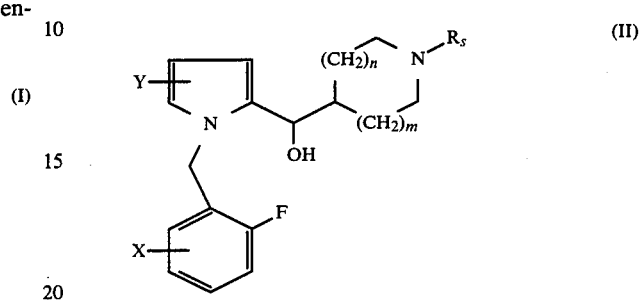

To the best of our knowledge the compounds of the present invention have not heretofore been described or suggested.

In the above definitions and as used throughout the specification and the appended claims the term "lower" means the group it is describing contains 1 to 4 carbon atoms. The term "alkyl" refers to a straight or branched chain hydrocarbon containing no unsaturation e.g. methyl, ethyl, n-propyl, isoopropyl, tertiary-butyl, etc. The term "halogen" means fluorine, chlorine, bromine or iodine.

Where an optical isomerism exists, a given chemical name or formula shall encompass all optical isomers and mixtures thereof including the racemic mixture thereof throughout the specification and the appended claims. The same is true of stereo isomers including geometrical isomers.

The present invention will be described in detail below with a particular emphasis on the situation where m and n are both 1, and X and Y are both hydrogen in Formulas I and II. Thus, the synthetic steps will be described below with reference to compounds of Formulas Ia and IIa below, but the person skilled in the art will readily recognize that Compounds I and II can be prepared by simple modifications of the synthetic steps described below.

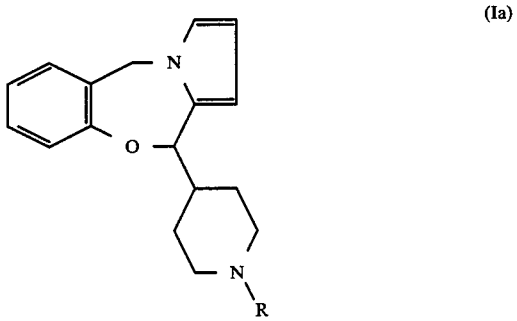

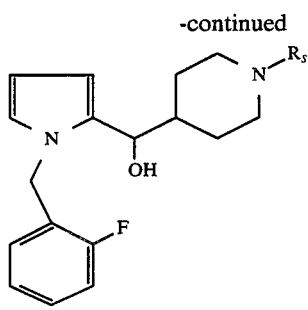

(IIa)

Compounds Ia and IIa may be prepared by following one or more of the following steps. Throughout the description of the synthetic steps, the same symbols shall have the same meanings unless otherwise indicated. Thus, the symbols n, k, W, X, Y, Z, R and $R_s$ are as defined earlier, R' shall mean loweralkylene, and the symbols R", R'" and Hal used hereinbelow shall have the respective meanings as defined at their first occurrences unless otherwise indicated.

STEP A

Compound III is reacted with a Grignard reagent IV and the product is hydrolyzed to afford Compound IIb. The symbol "Hal" shall mean chlorine or bromine.

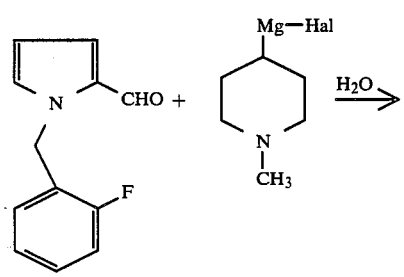

(III)     (IV)

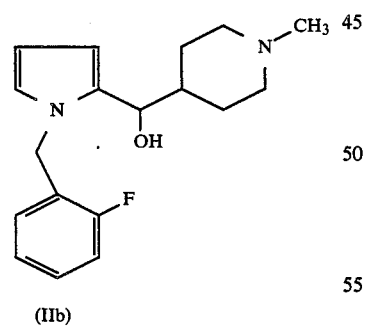

(IIb)

Said Grignard reagent IV is prepared for instance by reacting 1-methyl-4-chloropiperidine with magnesium in a suitable solvent such as THF and refluxing the mixture for a suitable length of time such as one hour. Typically, the Grignard reaction is conducted by adding a solution of Compound III in a suitable solvent such as THF to the solution of the Grignard reagent IV and stirring the mixture under reflux for a suitable length of time such as one hour. Hydrolysis of the reaction product affords Compound IIb.

STEP B

Compound IIb is reacted with a strong base such as NaH in a suitable solvent such as benzene/DMF mixture to afford Compound V by cyclization reaction. A typical reaction condition is stirring the reaction mixture in benzene/DMF at 90° C. for one hour.

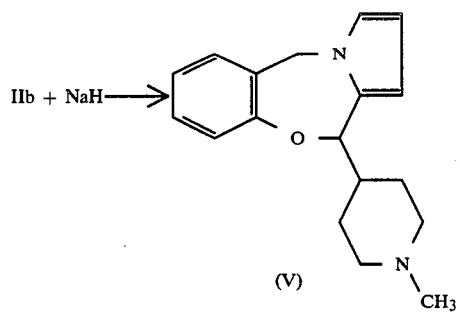

(V)

STEP C

Compound V is reacted with cyanogen bromide preferably in the presence of milled $K_2CO_3$ in a suitable solvent such as chloroform to afford Compound VI. A typical reaction condition is stirring the reaction mixture at 60° C. for two hours.

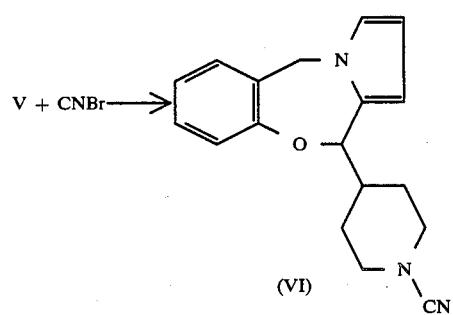

(VI)

STEP D

Compound VI is reacted with hydroxylamine hydrochloride in a suitable solvent such as DMF to afford Compound VII. A typical reaction condition is stirring the reaction mixture at 100° C. for two hours.

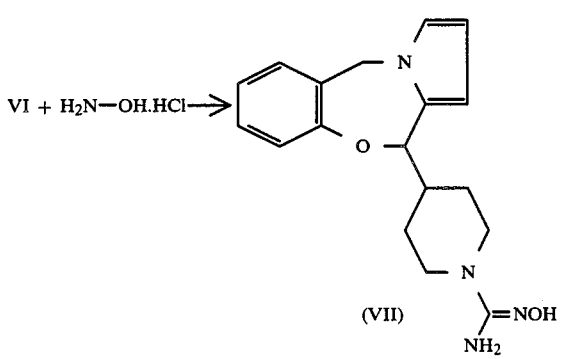

(VII)

STEP E

Compound IIc shown below is reacted with a strong base such as NaH in a suitable solvent such as benzene/DMF to afford Compound VIII.

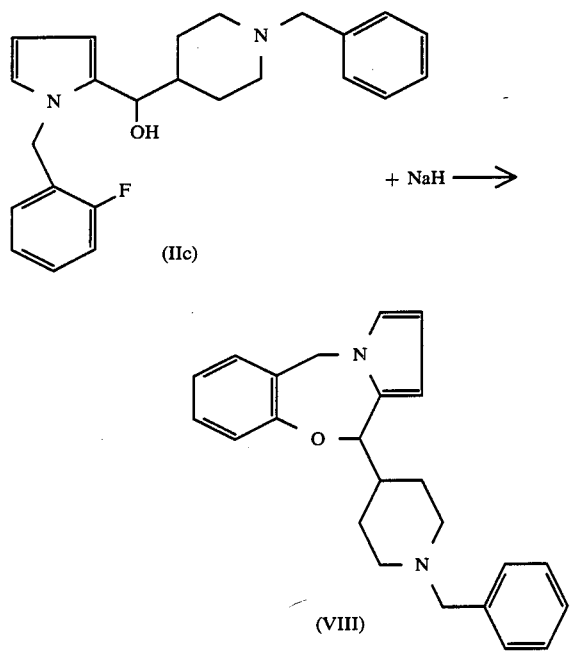

A typical reaction condition is stirring the mixture at 80° C. for three hours. Said Compound IIc is obtained from Compound III and a Grignard reagent of the formula

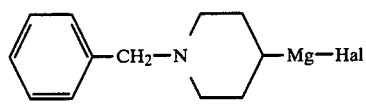

in the same manner as described in STEP A.

STEP F

Compound VIII is subjected to hydrogenolysis to afford Compound IX.

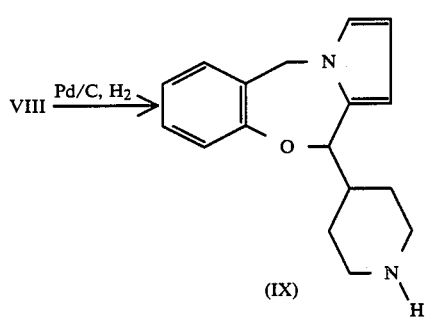

A typical reaction condition is shaking a solution of Compound VIII in a suitable solvent such as isopropanol at 50° C. in the presence of a suitable catalyst such as Pd/C under a hydrogen pressure (e.g. 50 psi) for six hours.

STEP G

Compound IX is reacted with a phenylisocyanate of the formula below in a suitable solvent such as benzene to afford Compound X. A typical reaction condition is stirring the reaction mixture at 65° C. for 1 hour.

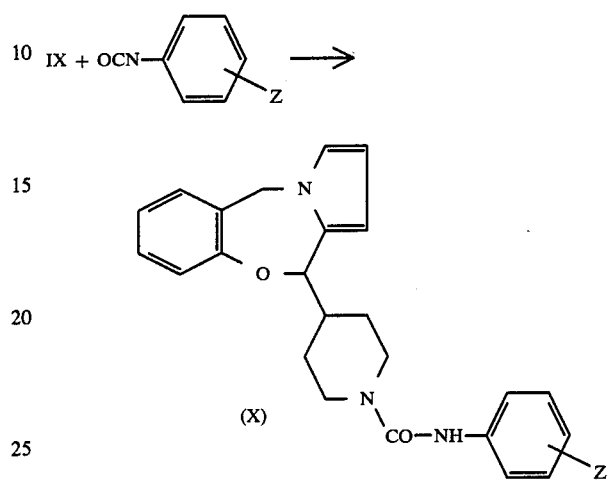

STEP H

Compound IX is reacted with an alkyl chloride or bromide of Formula R''-Hal (XI) to afford Compound XII.

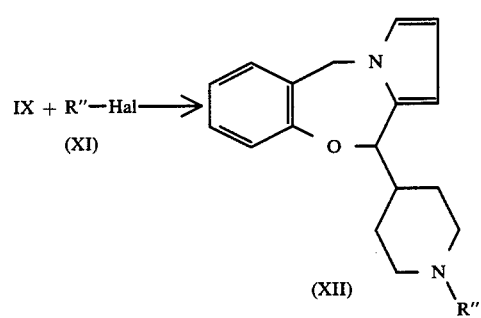

In the above equation, R'' is an unsubstituted loweralkyl or substituted loweralkyl having one to three substituents each of which being independently cyano, hydroxy, cyclohexyl, furyl, thienyl,

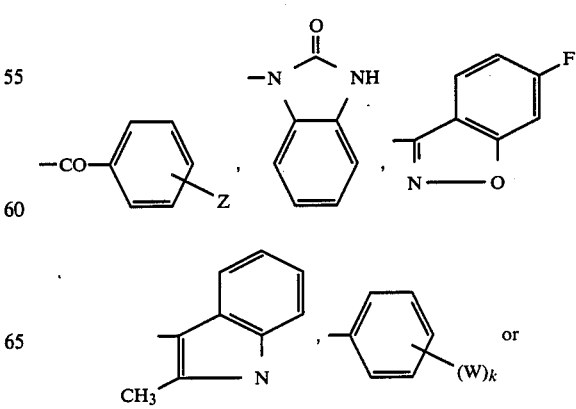

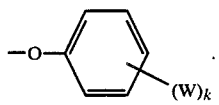

Usually the reaction is conducted in the presence of K₂CO₃ and a small amount of KI in a suitable solvent such as DMF. Although the reaction conditions vary depending upon the particular reactant, a typical reaction condition is stirring the reaction mixture at a temperature of 70°–90° for 1–10 hours.

Another example of suitable solvent is butyl acetate. Depending upon the reactivity of the system, the reaction may require a more severe condition such as refluxing in butyl acetate for 50 hours.

STEP I

As an alternative to STEP H, Compound XII (except where R" is a loweralkyl group substituted with

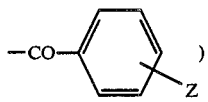

may be obtained from Compound IX in two steps. Firstly, Compound IX is reacted with an acyl chloride or bromide of the formula R'''CO-Hal to afford Compound XIII where R'''CO is such that if reduced to R'''CH₂, it corresponds to R" defined above. Said reaction is conducted usually in the presence of triethylamine in a suitable solvent such as dichloromethane. A typical reaction condition is stirring the reaction mixture at 0°–25° C. for 0.5–10 hours. The resultant amide Compound XIII is isolated. Secondly, Compound XIII is reduced with a suitable reagent such as lithium aluminum hydride in a suitable medium such as anhydrous THF to afford Compound XII. A typical reaction condition is stirring the reaction mixture at room temperature for a few hours.

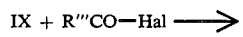

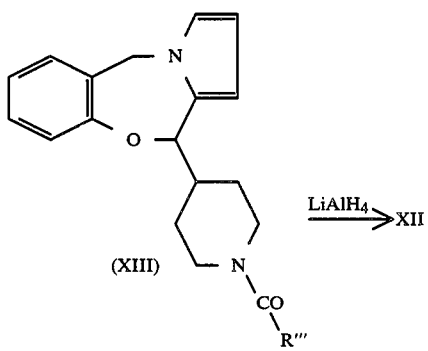

Thus, novel compounds of formula XIII of this invention are useful as intermediates for preparing Compounds XII of this invention.

STEP J

As an alternative to STEP H or I, Compound IX is reacted with a methane sulfonate compound of Formula XIV below to afford Compound XII.

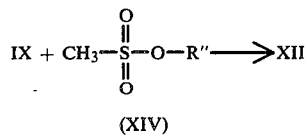

Usually the reaction is conducted in the presence of K₂CO₃ in a suitable solvent such as DMF. A typical reaction condition is stirring the mixture at 70°–90° C. for several hours.

STEP K

Compound IX is reacted with a compound of Formula XV to afford Compound XVI:

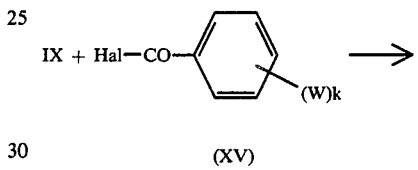

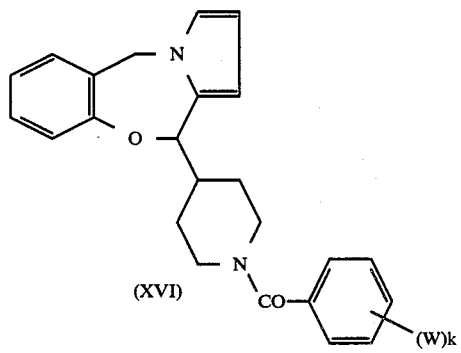

Said reaction is conducted usually in the presence of triethylamine in a suitable solvent such as dichloromethane. A typical reaction condition is stirring the reaction mixture at room temperature usually for less than one hour.

STEP L

As an alternative to STEP H, where R" is

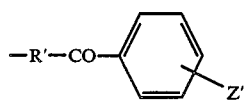

Compound IX is reacted with a compound of Formula XVII to afford Compound XVIII. Usually said reaction is conducted in the presence of K₂CO₃ in a suitable solvent such as DMF. A typical reaction condition is stirring the reaction mixture at room temperature for 24 hours.

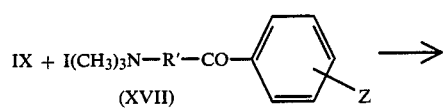 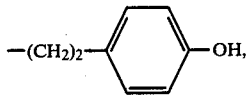

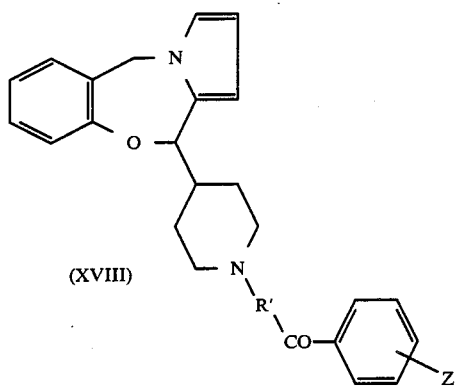

(XVIII)

STEP M

Compound XVIII obtained from STEP L or STEP H is reacted with cyclohexyl magnesium chloride or bromide and the product is hydrolyzed to afford Compound XIX. A typical condition of the Grignard reaction is stirring the reaction mixture in a suitable solvent such as ether at room temperature for one hour.

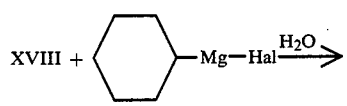

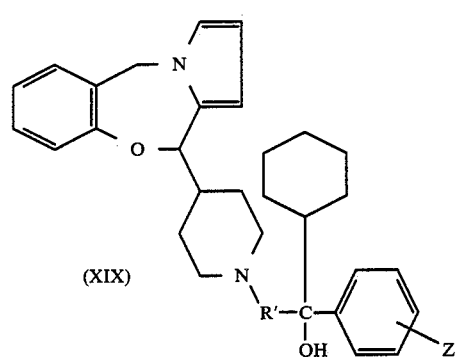

(XIX)

STEP N

Compound VI is subjected to hydrogenolysis by use of a suitable reagent such as LiAlH$_4$ to afford Compound IX as a major product. Said hydrogenolysis reaction is conducted in a suitable solvent such as THF, a typical reaction condition being refluxing the reaction mixture (70° C.) for two hours. This step may be regarded as an alternative to STEP F for preparing Compound IX.

VII+LiAlH$_4$→IX

STEP O

As an alternative to STEP H, where R'' is $-(CH_2)_2-$⟨⟩$-OH$,

Compound XX obtained from one of the preceding steps is subjected to hydrogenolysis to afford Compound XXI. Typically, said hydrogenolysis reaction is conducted by use of a suitable catalyst such as Pd/C under a hydrogen pressure in a suitable solvent such as isopropanol A typical reaction condition is shaking the mixture at room temperature for 24 hours.

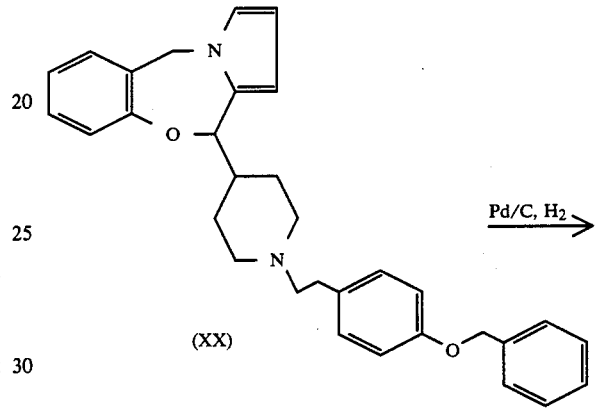

(XX)

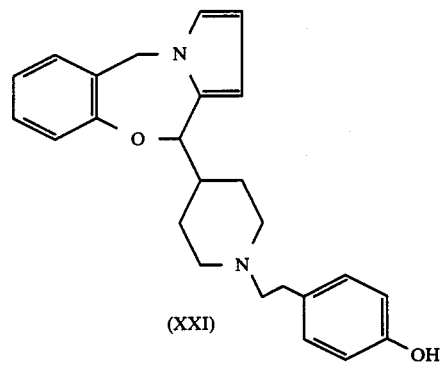

(XXI)

STEP P

As an alternative to STEP F, Compound IX, may be obtained by the following two-step reaction sequence. Firstly, Compound V is reacted with 2,2,2-trichloroethyl chloroformate to afford Compound XXII. Usually said reaction is conducted in the presence of K$_2$CO$_3$ in a suitable solvent such as dichloromethane, a typical reaction condition being stirring the reaction mixture at room temperature for 30 hours.

Secondly, glacial acetic acid and activated zinc metal are added to a solution of Compound XXII in a suitable solvent such as THF, and the mixture is stirred, typically at room temperature for ½ hour to afford Compound IX.

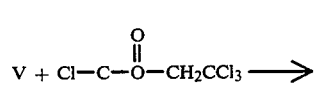

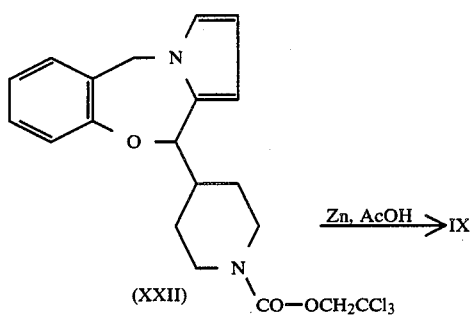

(XXII)

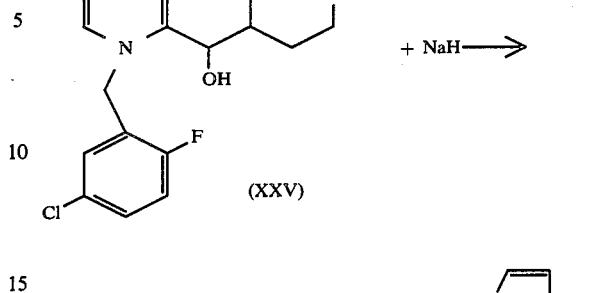

(XXV)

As mentioned earlier, Compounds I and II can be prepared by simple modifications of the synthetic steps described above. Thus, for instance, by cyclizing Compound XXIII in the same manner as described in STEP B, one can prepare Compound XXIV below. Said Compound XXIII

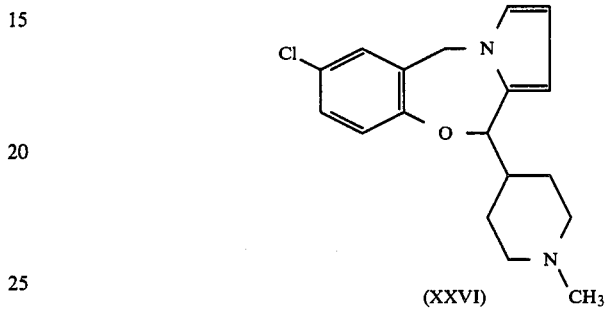

(XXVI)

Similarly, by cyclizing Compound XXVII below, one can obtain Compound XXVIII below.

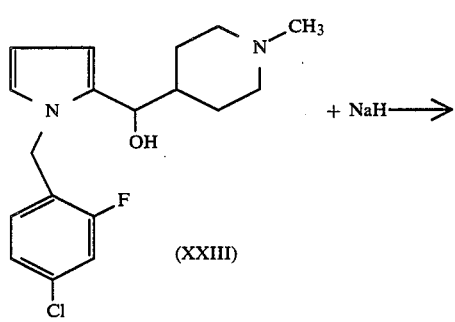

(XXIII)

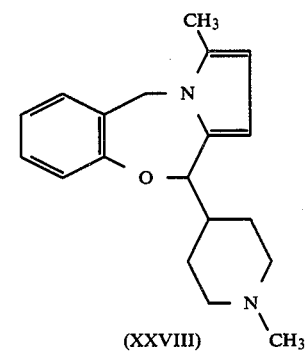

(XXVII)

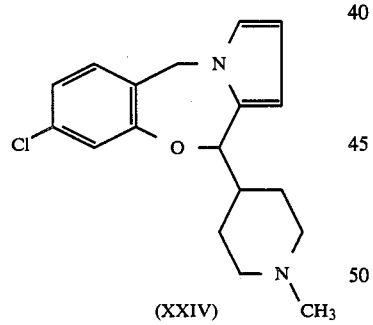

(XXIV)

can be prepared from

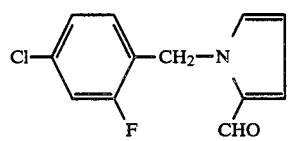

and the Grignard reagent IV in the same manner as described in STEP A.

Similarly, by cyclizing Compound XXV below, one can obtain Compound XXVI below.

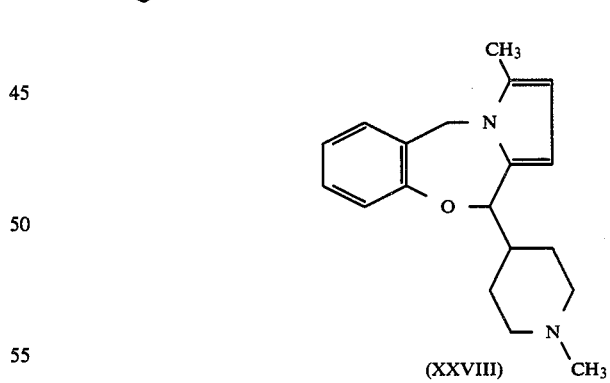

(XXVIII)

Said Compound XXVII can be obtained from 1-(2-fluorobenzyl)-5-methylpyrrol-2-carboxaldehyde and Grignard reagent IV in the same manner as STEP A.

Similarly, application of STEP P to Compound XXVI affords Compound XXIX below.

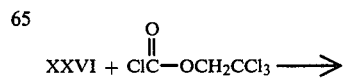

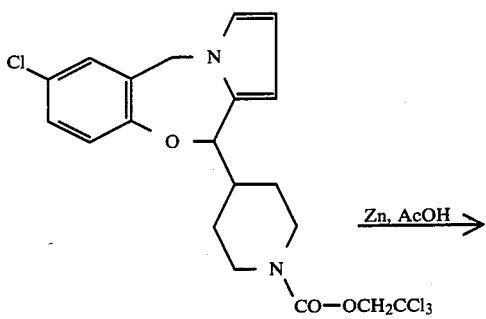

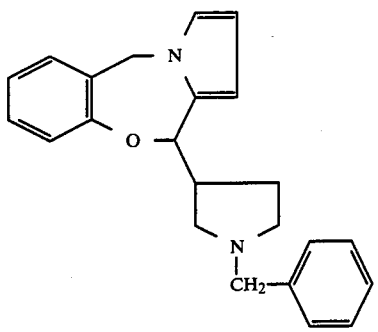

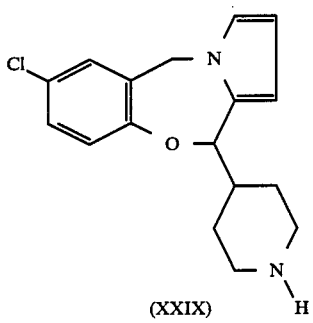

(XXIX)

STEP Q

Compound II wherein m=1 and n=0, can be obtained by the following methods.

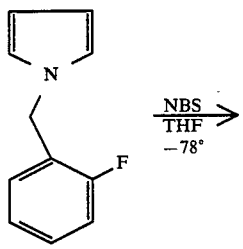

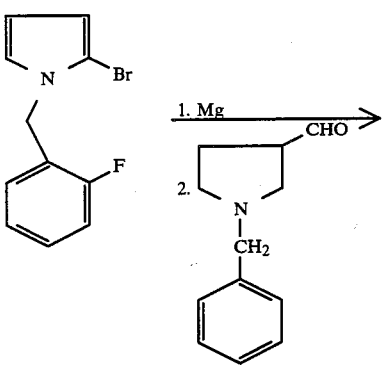

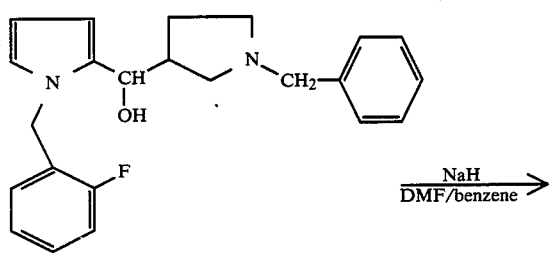

N-(o-fluorobenzylpyrrole) is brominated with N-bromosuccinimide the give the 2-bromopyrrole, which is converted to the Grignard reagent with magnesium in THF/ether, then reacted with N-benzylpyrrolidine-3-carboxaldehyde to give the secondary alcohol. Cyclization to the 11-(pyrrolidin-3-yl)-5H,11H-pyrrolo[2,1-c][1,4]benzoxazepine is carried out in a manner similar to the corresponding piperidines, using a strong base such as NaH in a suitable solvent such as benzene/DMF.

Once Compound II is obtained, one can prepare Compounds I by utilizing the synthetic steps described above.

All other starting materials shown above are either known compounds or easily prepared by routine methods known to the art from readily available materials.

Compounds of the present invention are useful as antipsychotic agents.

Antipsychotic activity is determined in the climbing mice assay by methods similar to those described by P. Protais, et al., Psychopharmacol., 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally 30 minutes prior to the apomorphine challenge at a screening dose of 10 mg/kg.

For evaluation of climbing, 3 readings are taken at 10, 20 and 30 minutes after apomorphine administration according to the following scale:

| Climbing Behavior | Score |
|---|---|
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless, over longer periods of time. By contrast, climbs due to mere motor stimulation usually last only a few seconds.

The climbing scores are individually totaled (maximum score: 6 per mouse over 3 readings) and the total score of the control group (vehicle intraperitoneally—apomorphine subcutaneously) is set to 100%. $ED_{50}$ values with 95% confidence limits, calculated by a linear regression analysis of some of the compounds of this invention are presented in Table 1.

TABLE 1

| COMPOUND | ANTIPSYCHOTIC ACTIVITY (Climbing Mice Assay) $ED_{50}$ mg/kg ip |
|---|---|
| 11-{1-[3-(1,3-Dihydro-2-oxo-2H—benzimidazol-1-yl)propyl]piperidin-4-yl}-5H,11H—pyrrolo[2,1-c][1,4]benzoxazepine oxalate | 0.7 |
| 11-{1-[3-(6-Fluoro-1,2-benzisoxazol-3-yl)-propyl]piperidin-4-yl}-5H,11H—pyrrolo[2,1-c][1,4]benzoxazepine oxalate | 2.1 |
| 11-{1-[2-(Phenyl)ethyl]piperidin-4-yl}-5H,11H—pyrrolo[2,1-c][1,4]benzoxazepine oxalate | 3.1 |
| 11-{1-[3-(2-Methylindol-3-yl)propyl]-piperidin-4-yl}-5H,11H—pyrrolo[2,1-c][1,4]-benzoxazepine oxalate | 2.3 |
| 11-{1-[2-(1,3-Dihydro-2-oxo-2H—benzimidazol-1-yl)ethyl]piperidin-4-yl)-5H,11H—pyrrolo[2,1-c][1,4]benzoxazepine oxalate | 3.2 |
| 11-{1-[2-(4-Methoxyphenyl)ethyl]-piperidin-4-yl}-5H,11H—pyrrolo[2,1-c][1,4]-benzoxazepine oxalate | 0.3 |
| 11-{1-[2-(4-Fluorophenyl)ethyl]-piperidin-4-yl}-5H,11H—pyrrolo[2,1-c][1,4]-benzoxazepine oxalate | 3.1 |
| 11-{1-[2-(4-Methylphenyl)ethyl]piperidin-4-yl}-5H,11H—pyrrolo[2,1-c][1,4]benzoxazepine | 1.2 |
| 11-{1-[3-(Phenyl)propyl]piperidin-4-yl}-5H,11H—pyrrolo[2,1-c][1,4]benzoxazepine oxalate | 2.0 |
| 11-{1-[3-(Phenoxy)propyl]piperidin-4-yl}-5H,11H—pyrrolo[2,1-c][1,4]benzoxazepine | 1.2 |
| 11-{1-[2-(4-Ethoxyphenyl)ethyl]piperidin-4-yl}-5H,11H—pyrrolo[2,1-c][1,4-]benzoxazepine | 1.3 |
| 11-{1-[2-(4-Chlorophenyl)ethyl]piperidin-4-yl}-5H,11H—pyrrolo[2,1-c][1,4]benzoxazepine | 2.1 |
| 11-[1-(3-Phenylpropan-3-one)piperidin-4-yl]-5H,11H—pyrrolo[2,1-c][1,4]benzoxazepine oxalate | 1.6 |
| 11-{1-[2-(4-Nitrophenyl)ethyl]piperidin-4-yl}-5H,11H—pyrrolo[2,1-c][1,4]benzoxazepine | 3.5 |
| 11-{1-[2-(3,4-Dimethoxyphenyl)ethyl]-piperidin-4-yl}-5H,11H—pyrrolo[2,1-c][1,4]-benzoxazepine | 0.3 |
| 11-{1-[2-(4-Dimethylaminophenyl)ethyl]-piperidin-4-yl}-5H,11H—pyrrolo[2,1-c][1,4]-benzoxazepine | 1.2 |
| 11-[(1-Butyl)piperidin-4-yl]-5H,11H—pyrrolo[2,1-c][1,4]benzoxazepine | 3.8 |
| 11-{1-[2-(4-Hydroxyphenyl)ethyl]piperidin-4-yl}-5H,11H—pyrrolo[2,1-c][1,4]benzoxazepine | 0.3 |
| 11-{1-[2-(3-Methoxyphenyl)ethyl]piperidin-4-yl}-5H,11H—pyrrolo[2,1-c][1,4]benzoxazepine | 0.9 |
| 11-{1-[2-(2,3-Dimethoxyphenyl)ethyl]-piperidin-4-yl}-5H,11H—pyrrolo[2,1-c][1,4]-benzoxazepine fumarate | 3.0 |
| 11-{1-[3-(4-Chlorophenyl)propan-3-one)]-piperidin-4-yl}-5H,11H—pyrrolo[2,1-c][1,4]-benzoxazepine | 5.5 |
| 11-{1-[2-(2-Thienyl)ethyl]piperidin-4-yl}-5H,11H—pyrrolo[2,1-c][1,4]benzoxazepine | 1.8 |

Antipsychotic response is achieved when the compounds of this invention are administered to a subject requiring such treatment as an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and they do not, to any extent, limit the scope or practice of the invention.

Compounds of the present invention are useful as analgesic agents due to their ability to alleviate pain in mammals. The activity of the compounds is demonstrated in the 2-phenyl-1,4-benzoquinone-induced writhing test in mice, a standard assay for analgesia, [Proc. Soc. Exptl. Biol. Med., 95, 729 (1957)]. Table 2 shows a result of the test of the analgesic activities of some of the compounds of this invention.

TABLE 2

| COMPOUND | ANALGESIC ACTIVITY (Phenylquinone Writhing) $ED_{50}$ mg/kg sc |
|---|---|
| 11-{1-[3-(1,3-Dihydro-2-oxo-2H—benzimidazol-1-yl)propyl]piperidin-4-yl}-5H,11H—pyrrolo[2,1-c][1,4]benzoxazepine oxalate | 0.3 |
| 11-{1-[3-(6-Fluoro-1,2-benzisoxazol-3-yl)-propyl]piperidin-4-yl}-5H,11H—pyrrolo[2,1-c][1,4]benzoxazepine oxalate | 5.1 |
| 11-{1-[2-(1,3-Dihydro-2-oxo-2H—benzimidazol-1-yl)ethyl]piperidin-4-yl}-5H,11H—pyrrolo[2,1-c][1,4]benzoxazepine oxalate | 0.9 |
| 11-{1-[2-(4-Methoxyphenyl)ethyl]piperidin-4-yl}-5H,11H—pyrrolo[2,1-c][1,4]benzoxazepine oxalate | 0.3 |
| 11-{1-[3-(Phenoxy)propyl]piperidin-4-yl}-5H,11H—pyrrolo[2,1-c][1,4]benzoxazepine | 4.2 |
| 11-{1-[2-(4-Ethoxyphenyl)ethyl]piperidin-4-yl}-5H,11H—pyrrolo[2,1-c][1,4]benzoxazepine | 1.9 |
| 11-[1-(3-Phenylpropan-3-one)piperidin-4-yl]-5H,11H—pyrrolo[2,1-c][1,4]benzoxazepine oxalate | 1.6 |
| 11-{1-[2-(4-Nitrophenyl)ethyl]piperidin-4-yl]-5H,11H—pyrrolo[2,1-c][1,4]benzoxazepine | 4.1 |
| 11-{1-[2-(3,4-Dimethoxyphenyl)ethyl]-piperidin-4-yl}-5H,11H—pyrrolo[2,1-c][1,4]benzoxazepine | 0.1 |
| 11-{1-[2-(4-Dimethylaminophenyl)ethyl]-piperidin-4-yl}-5H,11H—pyrrolo[2,1-c][1,4]-benzoxazepine | 0.4 |
| 11-[(1-Butyl)piperidin-4-yl]-5H,11H—pyrrolo[2,1-c][1,4]benzoxazepine | 0.4 |

The compounds of the invention compare favorably with the well known analgesic compound ibuprofen, which, in a similar test exhibited an analgesic $ED_{50} = 10.4$ mg/kg, orally.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied to be between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspension may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:

[1-(2-Fluorobenzyl)-2-pyrryl]-[(1-methyl)piperidin-4-yl]methanol;

11-[(1-Methyl)piperidin-4-yl]-5H,11H-pyrrolo[2,1-c][1,4]benzoxazepine;

11-[(1-Carboxamidoxime)piperidin-4-yl]-5H,11H-pyrrolo[2,1-c][1,4]benzoxazepine;

11-[(1-Cyano)piperidin-4-yl]-5H,11H-pyrrolo[2,1-c][1,4]benzoxazepine;

11-[(1-Benyl)piperidin-4-yl]-5H,11H-pyrrolo[2,1-c][1,4]benzoxazepine;

11-(Piperidin-4-yl)-5H,11H-pyrrolo[2,1-c][1,4]benxoxazepine oxalate;

11-{[1-(4-bis-4-Fluorophenyl)butyl]piperidin-4-yl}-5H,11H-pyrrolo[2,1-c][1,4]benzoxazepine;

11-{1-[3-(1,3-Dihydro-2-oxo-2H-benzimidazol-1-yl)propyl]piperidin-4-yl}-5H,11H-pyrrolo[2,1-c][1,4]benzoxazepine oxalate;

11-{1-[3-(6-Fluoro-1,2-benzisoxazol-3-yl)propyl]piperidin-4-yl}-5H,11H-pyrrolo[2,1-c][1,4]benzoxazepine oxalate;

11-[(1-Propyl)piperidin-4-yl]-5H,11H-pyrrolo[2,1-c][1,4]benzoxazepine oxalate;

11-{1-[2-(Phenyl)ethyl]piperidin-4-yl}-5H,11H-pyrrolo[2,1-c][1,4]benzoxazepine oxalate;

11-{1-[3-(2-Methylindol-3-yl)propyl]piperidin-4-yl}-5H,11H-pyrrolo[2,1-c][1,4]benzoxazepine oxalate;

11-[1-(2,4,6-Trimethylbenzyl)piperidin-4-yl]-5H,11H-pyrrolo[2,1-c][1,4]benzoxazepine;

11-[1-(2-Furanylmethyl)piperidin-4-yl]-5H,11H-pyrrolo[2,1-c][1,4]benzoxazepine oxalate;

11-{1-[2-(1,3-Dihydro-2-oxo-2H-benzimidazol-1-yl)ethyl]piperidin-4-yl}-5H,11H-pyrrolo[2,1-c][1,4]benzoxazepine oxalate;

11-[(1-Ethyl)piperidin-4-yl]-5H,11H-pyrrolo[2,1-c][1,4]benzoxazepine oxalate;

11-[1-(3-Trifluoromethylbenzyl)piperidin-4-yl]-5H,11H-pyrrolo[2,1-c][1,4]benzoxazepine oxalate;

11-[1-(1-Methylethyl)piperidin-4-yl]-5H,11H-pyrrolo[2,1-c][1,4]benzoxazepine oxalate;

11-{1-[2-(4-Methoxyphenyl)ethyl]piperidin-4-yl}-5H,11H-pyrrolo[2,1-c][1,4]benzoxazepine oxalate;

11-[1-(4-Methoxybenzyl)piperidin-4-yl]-5H,11H-pyrrolo[2,1-c][1,4]benzoxazepine;

11-{1-[2-(4-Fluorophenyl)ethyl]piperidin-4-yl}-5H,11H-pyrrolo[2,1-c][1,4]benzoxazepine oxalate;

11-{1-[2-(Phenoxy)ethyl]piperidin-4-yl}-5H,11H-pyrrolo[2,1-c][1,4]benzoxazepine oxalate;

11-[1-(3,4-Dichlorobenzoyl)piperidin-4-yl]-5H,11H-pyrrolo[2,1-c][1,4]benzoxazepine;

11-[1-(4-Chlorobenzyl)piperidin-4-yl]-5H,11H-pyrrolo[2,1-c][1,4]benzoxazepine oxalate;

11-{1-[2-(4-Methylphenyl)ethyl]piperidin-4-yl}-5H,11H-pyrrolo[2,1-c][1,4]benzoxazepine 11-{1-[3-(Phenyl)propyl]piperidin-4-yl}-5H,11H-pyrrolo[2,1-c][1,4]benzoxazepine oxalate;

11-{1-[(3-Cyano-3,3-diphenyl)propyl]piperidin-4-yl}-5H,11H-pyrrolo[2,1-c][1,4]benzoxazepine oxalate;

11-{1-[3-(Phenoxy)propyl]piperidin-4-yl}-5H,11H-pyrrolo[2,1-c][1,4]benzoxazepine;

11-{1-[(2-Phenyl)propyl]piperidin-4-yl}-5H,11H-pyrrolo[2,1-c][1,4]benzoxazepine;

11-[1-(2-Fluorobenzyl)piperidin-4-yl]-5H,11H-pyrrolo[2,1-c][1,4]benzoxazepine;

11-{1-[(3-Cyclohexyl-3-hydroxy-3-phenyl)propyl]piperidin-4-yl}-5H,11H-pyrrolo[2,1-c][1,4]benzoxazepine maleate;

11-{1-[2-(4-Ethoxyphenyl)ethyl]piperidin-4-yl]-5H,11H-pyrrolo[2,1-c][1,4]benzoxazepine;

11-{1-[2-(4-Clorophenyl)ethyl]piperidin-4-yl]-5H,11H-pyrrolo[2,1-c][1,4]benzoxazepine;

11-[1-(3-Phenylpropan-3-one)piperidin-4-yl]-5H,11H-pyrrolo[2,1-c][1,4]benzoxazepine oxalate;

11-{1-[2-(4-Nitrophenyl)ethy]piperidin-4-yl}-5H,11H-pyrrolo[2,1-c][1,4]benzoxazepine;

11-[1-(3,4-Dichlorobenzyl)piperidin-4-yl]-5H,11H-pyrrolo[2,1-c][1,4]benzoxazepine;
11-{1-[2-(4-Benzyloxyphenyl)ethyl]piperidin-4-yl}-5H,11H-pyrrolo[2,1-c][1,4]benzoxazepine;
11-{1-[2-(3,4-Dichlorophenyl)ethyl]piperidin-4-yl}-5H,11H-pyrrolo[2,1c-][1,4]benzoxazepine;
11-{1-[2-(3,4-Dimethoxyphenyl)ethyl]piperidin-4-yl}-5H,11H-pyrrolo[2,1-c][1,4]benzoxazepine;
11-{1-[2-(4l -Dimethylaminophenyl)ethyl]piperidin-4-yl}-5H,11H-pyrrolo[2,1-c][1,4]benzoxazepine;
11-{1-[2-(2-Methoxyphenyl)ethyl]piperidin-4-yl}-5H,11H-pyrrolo[2,1-c][1,4]benzoxazepine;
11-[(1-Butyl)piperidin-4-yl]-5H,11H-pyrrolo[2,1-c][1,4]benzoxazepine;
11-{1-[2-(4-Hydroxyphenyl)ethyl]piperidin-4-yl}-5H,11H-pyrrolo[2,1-c][1,4]benzoxazepine;
11-{1-[2-(3-Methoxyphenyl)ethyl]piperidin-4-yl}-5H,11H-pyrrolo[2,1-c][1,4]benzoxazepine;
11-{1-[2-(2,3-Dimethoxyphenyl)ethyl]piperidin-4-yl}-5H,11H-pyrrolo[2,1-c][1,4]benzoxazepine fumarate;
11-{1-[2-(3-Trifluoromethylphenyl)ethyl]piperidin-4-yl}-5H,11H-pyrrolo[2,1-c][1,4]benzoxazepine;
11-{1-[2-(3-Chlorophenyl)ethyl]piperidin-4-yl}-5H,11H-pyrrolo[2,1-c][1,4]benzoxazepine;
11-{1-[2-(3,4,5-Trimethoxyphenyl)ethyl]piperidin-4-yl}-5H,11H-pyrrolo[2,1-c][1,4]benzoxazepine;
11-{1-[2-(4-Hydroxy-3-methoxyphenyl)ethyl]piperidin-4-yl}-5H,11H-pyrrolo[2,1-c][1,4]benzoxazepine;
8-Chloro-11-[(1-methyl)piperidin-4-yl]-5H,11H-pyrrolo[2,1-c][1,4]benzoxazepine;
11-{1-[2-(2-Thienyl)ethyl]piperidin-4-yl}-5H,11H-pyrrolo[2,1-c][1,4]benzoxazepine;
11-{1-[3-(4-Chlorophenyl)propan-3-one)]piperidin-4-yl}-5H,11H-pyrrolo[2,1-c][1,4]benzoxazepine;
11-{1-[2-(4-Trifluoromethylphenyl)ethyl]piperidin-4-yl}-5H,11H-pyrrolo[2,1-c][1,4]benzoxazepine;
11-{1-[2-(2-Fluorophenyl)ethyl]piperidin-4-yl}-5H,11H-pyrrolo[2,1-c][1,4]benzoxazepine;
11-{1-[3-(4-Fluorophenyl)propan-3-one]piperidin-4-yl}-5H,11H-pyrrolo[2,1-c][1,4]benzxazepine;
111 -{1-[4-(4-Fluorophenyl)butan-4-ol]piperidin-4-yl}-5H,11H-pyrrolo[2,1-c][1,4]benzoxazepine fumarate;
7-Chloro-11-[(1-methyl)piperidin-4-yl]-5H,11H-pyrrolo[2,1-c][1,4]benzoxazepine;
N-Phenyl-4-(5H,11H-pyrrolo[2,1-c][1,4]benzoxazepine-11-yl)-1-piperdine carboxamide;
7-Chloro-11-(piperidin-4-yl)-5H,11H-pyrrolo[2,1-c][1,4]benzoxazepine;
11-{1-[2-(2-Trifluoromethylphenyl)ethyl]piperidin-4-yl}-5H,11H-pyrrolo[2,1-c][1,4]benzoxazepine fumarate; and
3-Methyl-11-[(1-methyl)piperidin-4-yl]-5H,11H-pyrrolo[2,1-c][1,4]benzoxazepine The following examples are shown for the purpose of illustrating the present invention.

EXAMPLE 1

[1-(2-Fluorobenzyl)-2-pyrryl]-[(1-methyl)piperidin-4-yl]methanol

To magnesium turnings (2.43 g, 0.1 mole) in 15 ml THF was added a few drops of 1,2-dibromoethane, followed by a few drops of a solution of 4-chloro-1-methylpiperidine (reconverted from the HCl-salt, b.p. 163° C., 13.5 g, 0.1 mole) in 30 ml THF.

The reaction was initiated with heat, and a gentle reflux was maintained by addition of the 4-chloro-1-methylpiperidine solution over a period of thirty minutes. The mixture was refluxed for an additional hour, by which time it had turned cloudy.

The heat was removed, and to the warm solution was added a solution of 1-(2-fluorobenzyl)pyrrole-2-carboxaldehyde (10.1 g, 0.05 mole) in 40 ml THF in fifteen minutes (solution cleared-up), and the resultant solution stirred at reflux for an additional hour.

The mixture was evaporated to about half of its volume, poured into 500 ml iced-$NH_4Cl$ solution, stirred for fifteen minutes, and extracted with ether. The ether solution was washed twice with water and dried (saturated NaCl, anhydrous $MgSO_4$).

After filtering, the solvents were evaporated to an oil, which solidified upon trituration with petroleum ether to 11.6 g (77%) of a solid, m.p. 109°–112° C. A sample of this material was recrystallized from hexanes/ether (4:1) to yield crystals, m.p. 112°–114° C.

ANALYSIS: Calculated for $C_{18}N_{23}FN_2O$: 71.49%C; 7.67%H; 9.27%N; Found: 71.31%C; 7.75%H; 9.18%N.

EXAMPLE 2

11-[(1-Methyl)piperidin-4-yl]-5H,11H-pyrrolo[2,1-c][1,4]benzoxazepine

To a suspension of sodium hydride (2.0 g, 50% in oil, treated with hexanes, 0.04 mole) in 50 ml benzene was added a suspension of [1-(2-fluorobenzyl)-2-pyrryl]-[(1-methyl)piperidin-4-yl]methanol (10.0 g, 0.033 mole) in 100 ml benzene, followed by 50 ml dimethylformamide.

The mixture was heated to reflux and stirred at 90° C. for one hour. After cooling, the solvents were evaporated to a semi-solid, which was poured into 500 ml water, stirred for ten minutes and extracted with ether/ethyl acetate. The organic layer was washed twice with water and then dried (saturated NaCl, anhydrous $MgSO_4$).

After filtering, the solvents were evaporated to an oil, which solidified upon trituration with hexanes to 9.0 g (95%) of a solid, m.p. 100°–102° C. A sample of this material was recrystallized from hexanes/ether (3:1) to give crystals, m.p. 102°–103° C.

ANALYSIS: Calculated for $C_{18}H_{22}N_2O$: 76.56%C; 7.85%H; 9.92%N; Found: 76.39%C; 7.68%H; 9.90%N.

EXAMPLE 3

11-[(1-Cyano)piperidin-4-yl]-5H,11H-pyrrolo[2,1-c][1,4]benzoxazepine

Milled $K_2CO_3$ (25 g, 0.18 mole) was added to a solution of cyanogen bromide (10.6 g, 0.1 mole) in 100 ml chloroform, and the mixture was heated to reflux and a solution of 11-[(1-methyl)piperidin-4-yl]-5H,11H-pyrrolo[2,1-c][1,4]benzoxazepine (24 g, 0.085 mole) in 100 ml chloroform was added thereto over a period of one hour.

After stirring at reflux (60° C.) for two hours, the mixture was cooled, filtered, and the filtrate evaporated to 25 g of a solid, m.p. 80°–90° C. A 4.0 g portion of this material was recrystallized from hexanes/acetone (5:1) to yield 2.9 g (76%) of crystals, m.p. 120°–122° C.

ANALYSIS: Calculated for $C_{18}H_{19}N_3O$: 73.69%C; 6.53%H; 14.32%N; Found: 73.40%C; 6.58%H; 14.28%N.

EXAMPLE 4

11-[(1-Carboxamidoxime)piperidin-4-yl]-5H,11H-pyrrolo[2,1c][1,4]benzoxazepine To 50 ml DMF were added 11-[(1-cyano)piperidin-4-yl]-5H,11H-pyrrolo[2,1-c][1,4]benzoxazepine (6.5 g, 0.022 mole), hydroxylamine hydrochloride (2.6 g, 0.04 mole), and milled $K_2CO_3$ (9.7 g, 0.07 mole).

After stirring at 100° C. for two hours, the mixture was cooled, poured into 500 ml water and extracted with ethyl acetate. The organic layer was washed twice with water and dried (saturated NaCl, anhydrous $MgSO_4$).

After filtering, the solvent was evaporated to 3.4 g (47%) of a solid, m.p. 105° C. This material was recrystallized twice from hexanes/acetone (5:1) to yield 2.4 g of a solid, m.p. 170°–172° C.

ANALYSIS: Calculated for $C_{18}H_{22}N_4O_2$: 66.23%C; 6.80%H; 17.17%N; Found: 66.05%C; 6.86%H; 16.87%N.

EXAMPLE 5

111-[(1-Benzyl)piperidin-4-yl]-5H,11H-pyrrolo[2,1-c][1,4]benzoxazepine

To a suspension of NaH (2.4 g, 0.05 mole, 50% in oil, treated with hexanes) in 20 ml dry benzene, was added a solution of [(1-benzyl)piperidin-4-yl]-[1-(2-fluorobenzyl)-2-pyrryl]methanol (15.0 g, 0.04 mole; prepared from 1-(2-fluorobenzyl)pyrrole-2-carboxaldehyde and 1-benzyl-4-chloropiperidine in a manner substantially the same as described in Example 1) in 80 ml dry benzene followed by 25 ml DMF.

After stirring at 80° C. for three hours, the mixture was poured into 200 ml iced water, stirred for ten minutes and then diluted with 100 ml ether. The organic layer was collected, washed twice with water and dried (saturated NaCl, anhydrous $MgSO_4$).

After filtering, the solvents were evaporated to an oil, which solidified upon trituration with hexanes to 10.0 g (71%) of a solid, m.p. 111°–113° C. This material was recrystallized twice from hexanes to yield a solid, m.p. 113°–115° C.

ANALYSIS: Calculated for $C_{24}H_{26}N_2O$: 80.41%C; 7.31%H; 7.82%N; Found: 80.56%C; 7.37%H; 7.79%N.

EXAMPLE 6

11-(Piperidin-4-yl)-5H,11H-pyrrolo[2,1-c][1,4]benzoxazepine oxalate

To 2.0 g of 10% Pd/C was added a solution of 11-[(1-benzyl)piperidin-4-yl]-5H,11H-pyrrolo[2,1-c][1,4]benzoxazepine (5.0 g, 0.014 mole) in 100 ml isopropanol. The mixture was pressurized to 50 psi with hydrogen and then shaken on a Parr apparatus at 50° C. for six hours.

The solution was cooled, filtered and then evaporated to a clear glass, which was converted to an oxalate salt by the addition of an ethereal solution of oxalic acid to yield 4.2 g (84%) of a solid, m.p. 75°–170° C. This material was recrystallized from ethyl acetate/methanol (10:1) to yield crystals, m.p. 165°–170° C.

ANALYSIS: Calculated for $C_{17}H_{20}N_2O \cdot (CO_2H)_2$: 63.67%C; 6.19%H; 7.82%N; Found: 63.65%C; 6.41%H; 7.74%N.

EXAMPLE 7

11-{[1-bis-4-Fluorophenyl)butyl]piperidin-4-yl}-5H,11H-pyrrolo[2,1-c][1,4]benzoxazepine To 40 ml DMF were added 11-(piperidin-4-yl)-5H,11H-pyrrolo[2,1-c][1,4]benzoxazepine (3.0 g, 0.011 mole), 4-chloro-1-bis-(p-fluorophenyl)butane (3.0 g, 0.0106 mole), milled $K_2CO_3$ (10 g) and 0.01 g KI.

After stirring at 90° C. for two hours, the mixture was filtered, and the filtrate evaporated to an oil. This oil was stirred with 100 ml water for five minutes and then extracted with ether. The ether solution was washed twice with water and dried (saturated NaCl, anhydrous $MgSO_4$).

After filtering, the filtrate was acidified to pH 1 with an ethereal solution of oxalic acid. The resultant precipitate was collected and dried to yield 5.1 g (77%), m.p. 90°–120° C. This material was recrystallized twice from ethyl acetate/methanol/ether (10:1:5) to yield 3.5 g, m.p. 145°–147° C.

ANALYSIS: Calculated for $C_{33}H_{34}F_2N_2O \cdot (CO_2H)_2$: 69.75%C; 6.02%H; 4.65%N; Found: 69.41%C; 6.02%H; 4.57%N.

EXAMPLE 8

11-{1-[3-(1,3-Dihydro-2-oxo-2H-benzimidazol-1-yl)propyl]piperidin-4-yl}-5H,11H-pyrrolo[2,1-c][1,4]benzoxazepine oxalate To 50 ml dry DMF were added 11-(piperidin-4-yl)-5H,11H-pyrrolo[2,1-c][1,4]benzoxazepine (5.0 g, 0.0186 mole), 1-(3-chloropropyl)-1,3-dihydro-2H-benzimidazol-2-one (4.0 g 0.019 mole), milled $K_2CO_3$ (10 g, 0.07 mole) and KI (0.01 g).

After stirring at 90° C. for two hours, the mixture was filtered, and the filtrate was evaporated to an oil. The oil was stirred with 100 ml water for five minutes, and then extracted with ether/ethyl acetate. The organic layer was washed twice with water and once with saturated sodium chloride, and then dried over anhydrous $MgSO_4$.

After filtering, the solution was acidified with an ethereal solution of oxalic acid to pH 1, and the resultant precipitate was collected and dried to yield 2.4 g (24%), d @ 130° C. This material was recrystallized from ethyl acetate/methanol/ether (10:1:5) to yield 2.1 g of crystals, d @ 135°–138° C.

ANALYSIS: Calculated for $C_{27}H_{30}N_4O_2 \cdot (CO_2H)_2$: 65.40%C; 6.06%H; 10.52%N; Found: 65.25%C; 6.10%H; 10.46%N.

EXAMPLE 9

11-{1-[3-(6-Fluoro-1,2-benzisoxazol-3-yl)propyl]piperidin-4-yl}-5H,11H-pyrrolo[2,1-c][1,4]benzoxazepine oxalate To 50 ml dry DMF were added 11-(piperidin-4-yl)-5H,11H-pyrrolo[2,1-c][1,4]benzoxazepine (3.0 g, 0.0112 mole), 3-(3-chloropropyl)-6-fluoro-1,2-benzisoxazole (4.2 g, 0.02 mole), milled $K_2CO_3$ (10 g, 0.07 mole) and KI (0.01 g).

After stirring at 90° C. for two hours, the mixture was filtered, and the filtrate was evaporated to an oil. The oil was stirred with 100 ml water and extracted with ether/ethyl acetate. The organic extracts were washed twice with water and dried (saturated NaCl, anhydrous $MgSO_4$).

After filtering, the solvents were evaporated to an oil, which was dissolved in ether and filtered. The solution was acidified to pH 1 with an ethereal solution of oxalic acid. The resultant precipitate was collected and dried to yield 2.3 g (38%), d @ 110° C. This material was recrystallized from ethyl acetate/methanol/ether (10:1:2) to yield a precipitate, d @ 145° C.

ANALYSIS: Calculated for $C_{27}H_{28}FN_3O_2 \cdot (CO_2H)_2$: 65.03%C; 5.65%H; 7.85%N; Found: 64.75%C; 5.63%H; 7.73%N.

EXAMPLE 10

11-[(1-Propyl)piperidin-4-yl]-5H,11H-pyrrolo[2,1-c][1,4]benzoxazepine oxalate

To 50 ml dry dichloromethane were added 11-(piperidin-4-yl)-5H,11H-pyrrolo[2,1-c][1,4]benzoxazepine (5.0 g, 0.0186 mole) and triethylamine (2.8 ml, 0.02 mole). To this solution was added at ice temperature a solution of propionyl chloride (1.8 ml, 0.02 mole) in 10 ml dichloromethane dropwise in about ten minutes.

After stirring at ambient temperature for twenty hours, the mixture was washed twice with water and dried (saturated NaCl, anhydrous $MgSO_4$). After filtering, the solvent was evaporated to yield 6 g of an oil.

To a cold suspension of $LiAlH_4$ (1.5 g, 0.04 mole) in 50 ml dry THF was added a solution of the amide (6 g, 0.018 mole) in 50 dry THF dropwise in ten minutes. After stirring at ambient temperature for twenty-four hours, the mixture was cooled, diluted with 100 ml ether and then quenched with 10 ml saturated $NH_4Cl$ solution. After filtering, the filtrate was acidified to pH 1 with ethereal oxalic acid, and the resultant precipitate collected and dried to yield 2.2 g, (30%), d @ 180° C. This material was recrystallized from ethyl acetate/methanol/ether (10:1:5), to yield a solid, d @ 185° C.

ANALYSIS: Calculated for $C_{20}H_{26}N_2O \cdot (CO_2H)_2$: 65.98%C; 7.05%H; 7.00%N; Found: 66.27%C; 7.09%H; 6.90%N.

EXAMPLE 11

11-{1-[2-(Phenyl)ethyl]piperidin-4-yl}-5H,11H-pyrrolo[2,1-c][1,4]benzoxazepine oxalate To 50 ml DMF were added 11-(piperidin-4-yl)-5H,11H-pyrrolo[2,1-c][1,4]benzoxazepine (4.5 g, 0.017 mole), (2-bromoethyl)benzene (4.3 ml, 0.03 mole), milled $K_2CO_3$ (10.0 g, 0.07 mole) and KI (0.01 g). AFter stirring at 90° C. for four hours the mixture was cooled and filtered, and the filtrate was concentrated in vacuo to an oil. This oil was dissolved in ethyl acetate, washed twice with water and dried (saturated NaCl, anhydrous $MgSO_4$).

After filtering, the solvent was concentrated in vacuo to afford 4.8 g of a solid, m.p. 65° C., which was extracted with 300 ml of a hot mixture of hexanes/ether (2:1). This organic extract was acidified to pH 1 with ethereal oxalic acid and the resultant precipitate collected and dried to yield 2.7 g (34%) d @ 100° C. This material was recrystallized from ethyl acetate/methanol/ether (10:1:5) to yield a solid, d @ 135° C.

ANALYSIS: Calculated for $C_{25}H_{28}N_2O \cdot (CO_2H)_2$: 70.11%C; 6.54%H; 6.06%N; Found: 69.71%C; 6.48%H; 6.25%N.

EXAMPLE 12

11-{1-[3-(2-Methylindol-3-yl)propyl]piperidin-4-yl}-5H,11H-pyrrolo[2,1-c][1,4]benzoxazepine oxalate To 60 ml DMF were added 11-(piperidin-4-yl)-5H,11H-pyrrolo[2,1-c][1,4]benzoxazepine (4.8 g, 0.018 mole), 2-methyl-3-(3-phenylsulfonyl)propylindole (8.2 g, 0.025 mole) and milled $K_2CO_3$ (15 g 0.11 mole). After stirring at 90° C. for three hours, the mixture was filtered, and the filtrate concentrated in vacuo to an oil. This oil was stirred with water (100 ml) and extracted with ethyl acetate. The organic layer was washed twice with water and dried (saturated NaCl, anhydrous $MgSO_4$).

After filtering, the solvent was concentrated in vacuo to an oil, which was converted to the oxalate salt in ether/ethyl acetate solution. The resultant precipitate was collected, washed with ether and dried to yield 4.0 g (42%), d @ 110° C. This material was recrystallized twice from ethyl acetate/methanol/ether (10:1:3) to yield 2.3 g, d @ 132° C.

ANALYSIS: Calculated for $C_{29}H_{33}N_3O \cdot (CO_2H)_2$: 70.30%C; 6.66%H; 7.93%N; Found: 70.03%C; 6.65%H; 7.93%N.

EXAMPLE 13

11-[1-(2,4,6-Trimethylbenzyl)piperidin-4-yl]-5H,11H-pyrrolo[2,1-c][1,4]benzoxazepine To 60 ml DMF, was added 11-(piperidin-4-yl)-5H,11H-pyrrolo[2,1-c][1,4]benzoxazepine (5.0 g, 0.0186 mole), 2,4,6-trimethylbenzyl chloride (4.2 g, 0.025 mole), milled $K_2CO_3$ (15 g, 0.1 mole) and KI (0.01 g).

After stirring at 90° C. for three hours, the mixture was cooled and filtered, and the filtrate was evaporated to an oil. This oil was stirred with 100 ml water and extracted with ethyl acetate. The organic layer was washed twice with water and dried (saturated NaCl, anhydrous $MgSO_4$). After filtering, the solvent was evaporated to afford 6 g of a semi-solid, which was extracted with 200 ml hot hexanes. The hexane solution was concentrated to half its volume to afford a 3.0 g (40%) of a solid precipitate, m.p. 164°–166° C. The solid was recrystallized twice from hexanes to yield 2.3 g of crystals, m.p. 168°–169° C.

ANALYSIS: Calculated for $C_{27}H_{32}N_2O$: 80.96%C; 8.05%H; 7.00%N; Found: 80.78%C; 8.10%H; 7.17%N.

EXAMPLE 14

11-[1-(2-Furanylmethyl)piperidin-4-yl]-5H,11H-pyrrolo[2,1-c][1,4]benzoxazepine oxalate To a cold solution of 11-(piperidin-4-yl)-5H,11H-pyrrolo[2,1-c][1,4]benzoxazepine (5.5 g, 0.0205 mole) and triethylamine (4.3 ml, 0.03 mole) in 50 ml dichloromethane was added a solution of 2-furanoyl chloride (2.9 ml, 0.03 mole) over a perid of twenty minutes.

After stirring at ambient temperature for seven hours, the mixture was evaporated to a semi-solid, which was stirred with 100 ml water and extracted with ethyl acetate. The organic solution was washed successively with water (twice), 10% HCl solution and water, and then dried (saturated NaCl, anhydrous $MgSO_4$).

After filtering, the solvent was evaporated to afford about 7 g (90%) of a gum, which was identified as the intermediate amide.

To a suspension of lithium aluminum hydride (2.2 g, 0.03 mole, 50% in oil) in 50 ml dry THF was added a solution of the amide (5.0 g, 0.014 mole) in 100 ml THF.

After stirring at ambient temperature for four hours, the mixture was cooled, quenched with 25 ml saturated $NH_4Cl$ solution, and then diluted with ether (100 ml). After filtering, the solvents were evaporated to an oil, which was dissolved in ether, filtered and acidified with an ethereal solution of oxalic acid. The resultant precipitate was collected and dried to yield 3.2 g (37%), d @ 115° C. This material was recrystallized three times from ethyl acetate/methanol/ether (10:1:1) to yield 2.2 g of a solid, d @ 193° C.

ANALYSIS: Calculated for $C_{22}H_{24}N_2O_2.(CO_2H)_2$: 65.73%C; 5.98%H; 6.39%N; Found: 65.78%C; 6.13%H; 6.44%N.

EXAMPLE 15

11-{1-[2-(1,3-Dihydro-2-oxo-2H-benzimidazol-1-yl)ethyl]piperidin-4-yl}-5H,11H-pyrrolo[2,1-c][1,4]benzoxazepine oxalate To 50 ml DMF, were added 11-(piperidin-4-yl)-5H,11H-pyrrolo[2,1-c][1,4]benzoxazepine (4.0 g, 0.015 mole), 1-(2-chloroethyl)-1,3-dihydro-2H-benzimidazol-2-one (3.9 g, 0.02 mole), milled $K_2CO_3$ (20 g, 0.15 mole) and KI (0.01 g). After stirring at 80° C. for three hours, the mixture was cooled, filtered and evaporated to an oil, which was stirred with water and extracted with ethyl acetate. The ethyl acetate layer was washed twice with water and dried (saturated NaCl, anhydrous $MgSO_4$).

After filtering, the solvent was evaporated to afford 2.6 g of a solid, d @ 100° C., which was dissolved in ether/ethyl acetate and converted to 2.8 g (40%) of the oxalate salt, d @ 120° C. This material was recrystallized three times from ethyl acetate/methanol/ether (10:2:1) to yield a solid, d @ 145° C.

ANALYSIS: Calculated for $C_{26}H_{28}N_4O_2.(CO_2H)_2$: 64.85%C; 5.83%H; 10.81%N; Found: 64.82%C; 5.68%H; 11.07%N.

EXAMPLE 16

11-[(1-Ethyl)piperidin-4-yl]-5H,11H-pyrrolo[2,1-c][1,4]benzoxazepine oxalate

To a cold solution of 11-(piperidin-4-yl)-5H,11H-pyrrolo[2,1-c][1,4]benzoxazepine (6.7 g, 0.025 mole) and triethylamine (4.0 ml, 0.03 mole) in 50 ml dichloromethane was added a solution of acetyl chloride (2.0 ml, 0.03 mole) in 30 ml dichloromethane.

After stirring at ambient temperature for four hours, the solution was poured into 100 ml water, diluted with 100 ml ethyl acetate and stirred for five minutes. The organic layer was washed twice with water and dried (saturated NaCl, anhydrous $MgSO_4$).

After filtering, the solvent was evaporated to an oil, which upon trituration with ether/hexanes (1:5) resulted in 6.0 g (80%) of a solid, m.p. 100° C.

To a cold suspension of $LiAlH_4$ (4.0 g, 0.05 mole, 50% in oil) in 50 ml THF was added a solution of the amide (6.6 g, 0.021 mole) in 50 ml THF over a period of ten minutes. After stirring at ambient temperature for three hours, the mixture was cooled, quenched with 10 ml saturated $NH_4Cl$ solution, diluted with 200 ml ether and filtered. The organic layer was washed twice with water and dried (saturated NaCl, anhydrous $MgSO_4$).

After filtering, the solvents were evaporated to 7 g (2 g oil) of an oil, which was dissolved in ether and converted to the oxalate salt by adding an ethereal solution of oxalic acid. The resultant precipitate was collected and dried to yield 5.0 g (62%), m.p. 90° C. This material was recrystallized twice from ethyl acetate/methanol/ether (10:2:1) to yield a solid, d @ 140° C.

ANALYSIS: Calculated for $C_{19}H_{24}N_2O.(CO_2H)_2$: 65.26%C; 6.78%H; 7.25%N; Found: 65.01%C; 6.97%H; 7.40%N.

EXAMPLE 17

11-[1-(3-Trifluoromethylbenzyl)piperidin-4-yl]-5H,11H-pyrrolo[2,1-c][1,4]benzoxazepine oxalate To 50 ml DMF were added 11-(piperidin-4-yl)-5H,11H-pyrrolo[2,1-c][1,4]benzoxazepine (6.0 g, 0.022 mole), 3-trifluoromethylbenzyl chloride (5.0 g, 0.026 mole), milled $K_2CO_3$ (10 g, 0.07 mole) and KI (0.01 g).

After stirring at 90° C. for two hours, the mixture was cooled and filtered, and the filtrate was evaporated to an oil, which was stirred with water and extracted with ether/ethyl acetate. The organic extract was washed twice with water and dried (saturated NaCl, anhydrous $MgSO_4$).

After filtering, the solvents were evaporated to afford about 7 g of an oil, which was dissolved in ether, filtered and acidified with an ethereal oxalic acid solution to yield 5.2 g (46%) of precipitate, d @ 100° C. This material was recrystallized twice from ethyl acetate/methanol/ether (10:1:2) to yield a solid, d @ 128° C.

ANALYSIS: Calculated for $C_{25}H_{25}F_3N_2O.(CO_2H)_2$: 62.78%C; 5.27%H; 5.42%N; Found: 62.68%C; 5.31%H; 5.35%N.

EXAMPLE 18

11-[1-(1-Methylethyl)piperidin-4-yl]-5H,11H-pyrrolo[2,1-c][1,4]benzoxazepine oxalate To 50 ml DMF were added 11-(piperidin-4-yl)-5H,11H-pyrrolo[2,1-c][1,4]benzoxazepine (6.4 g, 0.024 mole), isopropyl bromide (2.8 ml, 0.03 mole), milled $K_2CO_3$ (10 g, 0.07 mole) and KI (0.01 g).

After stirring at 50° C. for one hour and at ambient temperature for two hours, the mixture was filtered, and the filtrate evaporated to an oil. This oil was stirred with water for five minutes and extracted with ether. The ether solution was washed twice with water and dried (saturated NaCl, anhydrous $MgSO_4$).

After filtering, the solution was acidified with ethereal oxalic acid, and the resultant precipitate collected and dried to yield 2.3 g (24%), d @ 115° C. This material was recrystallized twice from ethyl acetate/methanol/ether (10:1:1) to yield a solid, d @ 135° C.

ANALYSIS: Calculated for $C_{20}H_{26}N_2O.(CO_2H)_2$: 65.98%C; 7.05%H; 7.00%N; Found: 66.21%C; 6.76%H; 7.28%N.

EXAMPLE 19

11-{1-[2-(4-Methoxyphenyl)ethyl]piperidin-4-yl}-5H,11H-pyrrolo[2,1-c][1,4]benzoxazepine oxalate To a cold solution of 11-(piperidin-4-yl)-5H,11H-pyrrolo[2,1-c][1,4]benzoxazepine (2.57 g; 0.01 mole in 75 ml $CH_2Cl_2$) and 1.7 ml $Et_3N$ (0.012 mole) was slowly added a solution of p-methoxyphenacetyl chloride (2.22 g; 0.012 mole in 20 ml $CH_2Cl_2$). The mixture was brought to room temperature and stirred for 45 minutes.

The solution was then washed twice with water and dried (saturated NaCl, $MgSO_4$). This was filtered and concentrated to yield a solid, m.p. 50°–59° C. This was chromatographed by HPLC with $CH_2Cl_2$ followed by 1% MeOH/CH$_2$Cl$_2$. The amide was isolated as 3.47 g of an oil.

To a cold solution of 11-[1-(4-methoxyphenacetyl)-piperidin-4-yl]-5H,11H-pyrrolo[2,1-c][1,4]benzoxazepine (3.4 g; 0.008 mole in 50 ml THF) was added 9 ml of 1 molar lithium aluminum hydride solution in THF. The mixture was brought to room temperature and stirred for 1.5 hours.

The reaction mixture was cooled and a saturated NH$_4$Cl solution was added thereto until a precipitate fell out of the solution. This was filtered and washed with ethyl acetate. The combined organics were washed twice with water and dried (saturated NaCl, MgSO$_4$). This was filtered and concentrated to a solid which was dissolved in ether and filtered. An addition of ethereal oxalic acid gave 2.97 g (60%) of the oxalate salt as a solid. This was recrystallized twice from ethyl acetate/methanol (10:1) to give an analytically pure solid, m.p. 140°-142° C.

ANALYSIS: Calculated for C$_{26}$H$_{30}$N$_2$O$_2$.(CO$_2$H)$_2$: 68.27%C; 6.55%H; 5.69%N; Found: 67.96%C; 6.53%H; 5.64%N.

EXAMPLE 20

11-[1-(4-Methoxybenzyl)piperidin-4-yl]-5H,11H-pyrrolo[2,1-c][1,4]benzoxazepine

To a cold solution of 11-(piperidin-4-yl)-5H,11H-pyrrolo[2,1-c][1,4]benzoxazepine (8.0 g; 0.03 mole in 200 ml CH$_2$Cl$_2$) and triethylamine (4.7 ml; 0.034 mole) was added p-methoxybenzoyl chloride (5.86 g; 0.034 mole in 20 ml CH$_2$Cl$_2$). This was stirred at room temperature for one hour.

The reaction mixture was then washed twice with water and dried (saturated NaCl, MgSO$_4$). This was filtered and concentrated to an oil, which was used without further purification.

To a cold solution of 11-[1-(4-methoxybenzoyl)-piperidin-4-yl]-5H,11H-pyrrolo[2,1-c][1,4]benzoxazepine (13.0 g in 100 ml THF) was added 45 ml of a 1 molar lithium aluminum hydride solution in ethyl ether. This was stirred at room temperature for 2 hours.

The reaction was then quenched with saturated NH$_4$Cl, filtered, and the precipitate was washed with ethyl acetate. The organics were washed twice with water and dried (saturated NaCl, MgSO$_4$). This was filtered and concentrated to an oil. The amine was purified via HPLC (hexane/ethyl acetate/diethylamine; 60:40:1) to yield 3.55 g (30%) of a solid, m.p. 142.5°-145° C. This was recrystallized from isopropyl ether/methanol (10:1) to give an analytically pure solid, m.p. 145.5°-148° C.

ANALYSIS: Calculated for C$_{25}$H$_{28}$N$_2$O$_2$: 77.29%C; 7.26%H; 7.21%N; Found: 77.35%C; 7.29%H; 7.15%N.

EXAMPLE 21

11-{1-[2-(4-Fluorophenyl)ethyl]piperidin-4-yl}-5H,11H-pyrrolo[2,1-c][1,4]benzoxazepine oxalate To 70 ml DMF were added 11-(piperidin-4-yl)-5H,11H-pyrrolo[2,1-c][1,4]benzoxazepine (8.0 g, 0.03 mole), 4-fluorophenethyl chloride (6.3 g, 0.04 mole), milled K$_2$CO$_3$ (10.0 g, 0.07 mole) and KI (0.01 g).

After stirring at 90° C. for two hours, the mixture was poured into 500 ml iced water, stirred for five minutes and extracted with ethyl acetate. The ethyl acetate layer was washed twice with water and dried (saturated NaCl, anhydrous MgSO$_4$).

After filtering, the solvent was evaporated to about 9 g of an oil, which was purified via HPLC on silica gel using ethyl ether/hexanes (1:1) containing 0.5% diethylamine. The product fraction was evaporated to about 3.5 g of an oil, which was dissolved in ether. The solution was acidified with ethereal oxalic acid, and the resultant precipitate was collected and dried to yield 3.2 g (22%), d @ 128° C.

This material was recrystallized twice from ethyl acetate/methanol/ether (10:1:5) to yield a solid, d @ 128° C.

ANALYSIS: Calculated for C$_{25}$H$_{27}$FN$_2$O.(CO$_2$H)$_2$: 67.48%C; 6.08%H; 5.83%N; Found: 67.31%C; 6.16%H; 5.63%N.

EXAMPLE 22

11-{1-[2-(Phenoxy)ethyl]piperidin-4-yl}-5H,11H-pyrrolo[2,1-c][1,4]benzoxazepine oxalate To a cold solution of 11-(piperidin-4-yl)-5H,11H-pyrrolo[2,1-c][1,4]benzoxazepine (8.0 g, 0.03 mole) and triethylamine (4.2 ml, 0.03 mole) in 50 ml dichloromethane was added a solution of phenoxyacetyl chloride (4.2 ml, 0.03 mole) in 25 ml dichloromethane over a period of ten minutes.

After stirring at ambient temperature for twenty hours, the mixture was diluted with 50 ml ethyl acetate, washed twice with water and dried (saturated NaCl, anhydrous MgSO$_4$). After filtering, the solvents were evaporated to about 8 g of a solid, which was purified via HPLC on silica gel using ethyl acetate/hexanes (7:3). The product fraction was collected and evaporated to give 3.0 g (25%) of a solid, d @ 75° C.

To a solution of LiAlH$_4$ in THF (1M in THF, 15 ml, 0.015 mole) was added a solution of 11-[1-(phenoxyacetyl)piperidin-4-yl]-5H,11H-pyrrolo[2,1-c][1,4]benzoxazepine (3.0 g, 0.0075 mole) in 40 ml THF.

After stirring at ambient temperature for three hours, the mixture was cooled, quenched with 5 ml saturated NH$_4$Cl solution and filtered. The filtrate was diluted with 50 ml ethyl acetate, washed twice with water and dried (saturated NaCl, anhydrous MgSO$_4$).

After filtering, the solvents were evaporated to about 3 g of a gum, which was dissolved in ether. The solution was acidified to pH 1 with oxalic acid, and the resultant precipitate was collected and dried to yield 2.8 g (78%), d @ 140° C. This material was recrystallized from ethyl acetate/methanol/ether (10:1:5) to yield a solid, d @ 145° C.

ANALYSIS: Calculated for C$_{25}$H$_{28}$N$_2$O$_2$.(CO$_2$H)$_2$: 67.76%C; 6.32%H; 5.86%N; Found: 68.14%C; 6.56%H; 5.86%N.

EXAMPLE 23

11-[1-(3,4-Dichlorobenzoyl)piperidin-4-yl]-5H,11H-pyrrolo[2,1-c][1,4]benzoxazepine To a cold solution of 11-(piperidin-4-yl)-5H,11H-pyrrolo[2,1-c][1,4]benzoxazepine (10.4 g; 0.04 mole in 150 ml CH$_2$Cl$_2$) and 6.7 ml Et$_3$N (0.048 mole) was slowly added a solution of 3,4-dichlorobenzoyl chloride (10.05 g; 0.048 mole in 60 ml CH$_2$Cl$_2$). This was stirred at room temperature for 15 minutes.

The solution was then washed once with saturated Na$_2$CO$_3$ solution and twice with water and dried (saturated NaCl solution, anhydrous MgSO$_4$). This was filtered and concentrated to yield a semi-solid.

The amide was purified via HPLC (2% EtOAc/CH$_2$Cl$_2$) to yield 11.63 g (68%) of an analytically pure crystal, m.p. 90°-94° C.

ANALYSIS: Calculated for $C_{24}H_{22}Cl_2N_2O_2$: 65.31%C; 5.02%H; 6.35%N; Found: 65.23%C; 5.11%H; 6.23%N.

EXAMPLE 24

11-[1-(3,4-Dichlorobenzyl)piperidin-4-yl]-5H,11H-pyrrolo[2,1-c][1,4]benzoxazepine To a cooled solution of 11-[1-(3,4-dichlorobenzoyl)piperidin-4-yl]-5H,11H-pyrrolo[2,1-c][1,4]benzoxazepine (4.8 g; 0.011 mole in 100 ml THF) was added a 1 molar solution of lithium aluminum hydride in THF (17 ml, 0.017 mole). This was then stirred at room temperature for 1 hour.

The reaction was cooled and quenched with a saturated $NH_4Cl$ solution, filtered and diluted with ethyl acetate. The organics were washed twice with a dilute NaCl solution and dried (saturated NaCl solution, anhydrous $MgSO_4$). This was filtered and concentrated to yield an oil.

The amine was purified via flash chromatography to give 2.78 g (59%) of a solid, m.p. 94°–100° C. This was recrystallized twice from isopropyl ether to give an analytically pure solid, m.p. 96°–99° C.

ANALYSIS: Calculated for $C_{24}H_{24}Cl_2N_2O$: 67.45%C; 5.66%H; 6.55%N; Found: 67.32%C; 5.87%H; 6.45%N.

EXAMPLE 25

11-[1-(4-Chlorobenzyl)piperidin-4-yl]-5H,11H-pyrrolo[2,1-c][1,4]benzoxazepine oxalate To a cold solution of 11-(piperidin-4-yl)-5H,11H-pyrrolo[2,1-c][1,4]benzoxazepine (5.99 g; 0.022 mole in 80 ml $CH_2Cl_2$) and triethylamine (4.2 ml, 0.03 mole) was added a solution of p-chlorobenzoyl chloride (4.55 g; 0.026 mole in 20 ml $CH_2Cl_2$). This was stirred at room temperature for 15 minutes.

The reaction mixture was then washed once with saturated $Na_2CO_3$ solution and twice with water and dried (saturated NaCl, $MgSO_4$). This was filtered and concentrated to a solid, m.p. 55°–75° C., which was used without further purification.

To a cold solution of 11-[1-(4-chlorobenzoyl)piperidin-4-yl]-5H,11H-pyrrolo[2,1-c][1,4]benzoxazepine (8.9 g; 0.022 mole in 100 ml THF) was added 38 ml of 1 molar lithium aluminum hydride solution in THF. This was stirred at room temperature for 2.5 hours.

The reaction was quenched with saturated $NH_4Cl$, filtered and the precipitate was washed with ethyl acetate. The organics were washed twice with water and dried (saturated NaCl, $MgSO_4$). This was filtered and concentrated to an oil.

The amine was purified via HPLC ($CH_2Cl_2$/EtOAc/$Et_2NH$; 95:5:0.5). Addition of etheral oxalic acid gave 5.7 g (52%) of the oxalate salt as a solid, m.p. 118°–125° C., decomp.

This was recrystallized from ethyl acetate/methanol (8:1) to give an analytically pure solid, m.p. 123°–128° C., decomp.

ANALYSIS:
Calculated for $C_{24}H_{25}ClN_2O \cdot (CO_2H)_2$: 64.66%C; 5.63%H; 5.80%N; Found: 65.01%C; 5.66%H; 5.80%N.

EXAMPLE 26

11-{1-[2-(4-Methylphenyl)ethyl]piperidin-4-yl}-5H,11H-pyrrolo[2,1-c][1,4]benzoxazepine To a cold solution of 11-(piperidin-4-yl)-5H,11H-pyrrolo[2,1-c][1,4]benzoxazepine (3.8 g; 0.014 mole in 60 ml $CH_2Cl_2$) and triethylamine (2.4 ml, 0.017 mole) was added a solution of p-methylphenylacetyl chloride (2.83 g, 0.017 mole in 15 ml $CH_2Cl_2$). This was stirred at room temperature for one hour.

The reaction was then diluted with additional $CH_2Cl_2$, washed twice with saturated $Na_2CO_3$ solution and once with water and dried (saturated NaCl solution, anhydrous $MgSO_4$).

This was filtered and concentrated to a solid, m.p. 55°–66° C., which was used without further purification.

To a cold solution of 11-[1-(4-methylphenacetyl)piperidin-4-yl]-5H,11H-pyrrolo[2,1-c][1,4]benzoxazepine (about 5.6 g; 0.014 mole in 100 ml THF) was added 20 ml of 1 molar lithium aluminum hydride solution in THF. The solution was brought to room temperature and stirred for two hours.

The reaction was then cooled and quenched with saturated $NH_4Cl$ solution, filtered and the precipitate was washed with ethyl acetate. The organics were washed twice with water and dried (saturated NaCl solution, anhydrous $MgSO_4$).

This was filtered and concentrated to an oil which was purified via HPLC (dichloromethane/ethyl acetate/diethylamine; 90:10:1) to give a solid, m.p. 104°–114° C. This was recrystallized from isopropyl ether to give 2.2 g (59%) of an analytically pure solid, m.p. 122°–123° C.

ANALYSIS: Calculated for $C_{26}H_{30}N_2O$: 80.79%C; 7.82%H; 7.25%N; Found: 81.08%C; 7.91%H; 7.15%N.

EXAMPLE 27

11-{1-[3-(Phenyl)propyl]piperidin-4-yl}-5H,11H-pyrrolo[2,1-c][1,4]benzoxazepine oxalate To 70 ml dry DMF were added 11-(piperidine-4-yl)-5H,11H-pyrrolo[2,1-c][1,4]benzoxazepine (6.0 g, 0.022 mole), 3-phenylpropylchloride (4.6 g, 0.03 mole), milled $K_2CO_3$ (10 g, 0.07 mole) and KI (0.01 g).

After stirring at 90° C. for three hours, the mixture was poured into 500 ml water, stirred for five minutes and extracted with ethyl acetate. The ethyl acetate solution was washed twice with water and dried (saturated NaCl, anhydrous $MgSO_4$).

After filtering, the solvent was evaporated to 8 g of an oil, which was purified via HPLC using ether/hexanes (1:1) containing 0.5% diethylamine. The resultant oil (6.0 g) was dissolved in ether and acidified to pH 1 with etheral oxalic acid. The resultant precipitate was collected and dried to yield 5.5 g (53%), d @ 105° C. This material was recrystallized three times from ethyl acetate/methanol/ether (5:1:50) to yield a solid, d @ 145° C.

ANALYSIS: Calculated for $C_{26}H_{30}N_2O \cdot (CO_2H)_2$: 70.56%C; 6.77%H; 5.88%N; Found: 70.53%C; 6.88%H; 5.83%N.

EXAMPLE 28

11-{1-[(3-Cyano-3,3-diphenyl)propyl]piperidin-4-yl}-5H,11H-pyrrolo[2,1-c][1,4]benzoxazepine oxalate To 75 ml DMF were added 11-(piperidin-4-yl)-5H,11H-pyrrolo[2,1-c][1,4]benzoxazpine (6.0 g, 0.022 mole), 4-bromo-2,2-diphenylbutyronitrile (7.5 g, 0.025 mole), milled $K_2CO_3$ (10 g, 0.07 mole) and KI (0.01 g).

After stirring at 90° C. for five hours, the mixture was poured into 500 ml water, stirred for five minutes and extracted with ethyl acetate. The ethyl acetate layer was washed twice with water and dried (saturated NaCl, anhydrous MgSO$_4$).

After filtering, the solvent was evaporated to about 13 g of an oil, which was purified by HPLC using ethyl acetate/dichloromethane (1:9) containing 0.5% diethylamine. The fractions were collected and evaporated to about 4 g of a semi-solid, which was dissolved in ether and acidified with etheral oxalic acid to pH 1. The resultant precipitate was collected and dried to yield 4.0 g (32%), d @ 40° C. This material was recrystallized twice from isopropanol/ether (1:20) to yield a solid, d @ 153° C.

ANALYSIS: Calculated for C$_{33}$H$_{33}$N$_3$O.(CO$_2$H)$_2$: 72.77%C; 6.11%H; 7.27%N; Found: 72.79%C; 6.13%H; 7.23%N.

EXAMPLE 29

11-{1-[3-(Phenoxy)propyl]piperidin-4-yl}-5H,11H-pyrrolo[2,1-c][1,4]benzoxazpine

To a solution of 11-(piperidin-4-yl)-5H,11H-pyrrolo[2,1-c][1,4]benzoxazepine (5.07 g, 0.019 mole in 75 ml DMF), 10 g milled K$_2$CO$_3$ and 10 mg KI, was added a solution of 3-phenoxypropylbromide (4.78 g, 0.022 mole in 20 ml DMF).

The mixture was heated at 85° C. for two hours. The reaction was then quenched into iced water and extracted twice with diethyl ether. The organics were washed with water and dried (saturated NaCl solution, anhydrous Na$_2$SO$_4$).

This was then filtered and concentrated to yield an oil. The amine was purified via HPLC (ethyl acetate/dichloromethane/diethylamine; 10:90:0.5) to yield 5.25 g (69%) of a solid, m.p. 90°-98° C. This was recrystallized from isopropyl ether to yield an analytically pure solid, m.p. 102°-103° C.

ANALYSIS: Calculated for C$_{26}$H$_{30}$N$_2$O$_2$: 77.58%C; 7.51%H; 6.96%N; Found: 77.29%C; 7.49%H; 6.90%N.

EXAMPLE 30

11-{1-[(2-Phenyl)propyl]piperidin-4-yl}-5H,11H-pyrrolo[2,1-c][1,4]benzoxazepine

To 75 ml dry DMF were added 11-(piperidin-4-yl)-5H,11H-pyrrolo[2,1-c][1,4]benzoxazepine (6.0 g, 0.022 mole), bromoisopropylbenzene (6.0 g, 0.03 mole), milled K$_2$CO$_3$ (10 g, 0.07 mole and KI (0.01 g).

After stirring at 90° C. for four hours, the mixture was poured into 500 ml water, stirred for five minutes and extracted with ether. The ether solution was washed twice with water and once with saturated NaCl, and dried over anhydrous MgSO$_4$.

After filtering, the solvent was evaporated to about 8 g of an oil, which was eluted on a silica gel column via HPLC using ethyl acetate/dichloromethane/diethylamine (3:97:0.5). The fractions were collected and evaporated to 3.0 g (35%) of a solid, m.p. 96°-99° C. This material was recrystallized from isopropyl ether to yield crystals, m.p. 107°-108° C.

ANALYSIS: Calculated for C$_{26}$H$_{30}$N$_2$O: 80.79%C; 7.82%H; 7.25%N; Found: 80.77%C; 7.75%H; 7.12%N.

EXAMPLE 31

11-[1-(2-Fluorobenzyl)piperidin-4-yl]-5H,11H-pyrrolo[2,1-c][1,4]benzoxazepine

To a solution of 11-(piperidin-4-yl)-5H,11H-pyrrolo[2,1-c][1,4]benzoxazpine (5.0 g; 0.010 mole in 75 ml DMF) and 10 g milled K$_2$CO$_3$ was added 2-fluorobenzyl chloride (3.18 g; 0.022 mole in 15 ml DMF). This was stirred at 85° C. for 1.5 hours.

The reaction was quenched into iced water and extracted twice with diethyl ether. The combined organics were washed with water and dried (saturated NaCl solution, anhydrous Na$_2$SO$_4$). This was concentrated to an oil.

The amine was purified via HPLC (ethyl acetate/dichloromethane/diethylamine; 5:95:0.5) to yield 5.6 g (75%) of a solid, m.p. 98°-110° C. This was recrystalized three times from isopropyl ether to yield an analytically pure solid, m.p. 110°-112° C.

ANALYSIS: Calculated for C$_{24}$H$_{25}$FN$_2$O: 76.57%C; 6.69%H; 7.44%N; Found: 76.48%C; 6.98%H; 7.35%N.

EXAMPLE 32

11-{1-[2-(4-Ethoxyphenylethyl)]piperidin-4-yl}-5H,11H-pyrrolo[2,1-c][1,4]benzoxazepine To a solution of 11-(piperidin-4-yl)-5H,11H-pyrrolo[2,1-c][1,4]benzoxazepine (5.5 g, 0.02 mole in 100 ml DMF), 10 g K$_2$CO$_3$ and 0.1 g KI was added p-ethoxyphenethyl chloride (4.25 g, 0.023 mole). The mixture was then heated to 80° C. bath temperature and stirred for 3 hours.

Water was added to the reaction mixture to quench the reaction and the mixture was extracted three times with diethyl ether. The combined organics were washed once with water and dried (saturated NaCl solution, anhydrous MgSO$_4$).

This was filtered and concentrated to yield an oil. The amine was purified via HPLC (ethyl acetate/dichloromethane/diethylamine; 8:92:0.5) to yield 2.42 g (29%) of a solid, m.p. 114°-117° C. This was recrystallized from isopropyl ether/hexane (1:1) to yield an analytically pure solid, m.p. 116°-117° C.

ANALYSIS Calculated for C$_{27}$N$_{32}$N$_2$O$_2$: 77.85%C; 7.74%H; 6.72%N; Found: 77.85%C; 7.88%H; 6.63%N.

EXAMPLE 33

11-{1-[2-(4-Chlorophenylethyl)]piperidin-4-yl}-5H,11H-pyrrolo[2,1-c][1,4]benzoxazepine To a cooled mixture of 11-(piperidin-4-yl)-5H,11H-pyrrolo[2,1-c][1,4]benzoxazepine (6.5 g, 0.024 mole in 100 ml dichloromethane) and Et$_3$N (5.6 ml, 0.04 mole) was added 4-chlorophenacetyl chloride (5.44 g, 0.029 mole in 10 ml dichloromethane). This was stirred at room temperature for ½ hour. The reaction mixture was then diluted with additional dichloromethane, washed once with water and dried (saturated NaCl solution, anhydrous MgSO$_4$).

This was filtered, concentrated and passed through a column of silica (THF) to yield an oil. This was used without further purification.

To a cooled solution of 11-[1-(4-chlorophenacetyl)-piperidin-4-yl]-5H,11H-pyrrolo[2,1-c][1,4benzoxazepine (about 7.0 g, 0.016 mole in 100 ml THF) was added a 1 molar solution of lithium aluminum hydride in THF (25 ml, 0.025 mole). This was stirred at room temperature for 3 hours.

The reaction was then quenched to a precipitate with saturated NH$_4$Cl solution, diluted with ethyl acetate, washed once with water and dried (saturated NaCl solution, anhydrous MgSO$_4$). This was filtered and concentrated to yield a semi-solid.

The amine was purified via HPLC (1% MeOH/dichloromethane) to yield 2.87 g (29%) of a solid, m.p. 115°-118° C. This was recrystallized from isopropyl ether to give an analytically pure solid, m.p. 117°–118.5° C.

ANALYSIS: Calculated for $C_{25}H_{27}ClN_2O$: 73.79%C; 6.69%H; 6.88%N, Found: 73.53%C; 6.65%H; 6.81%N.

EXAMPLE 34

11-{1-[3-(1-Phenylpropan-1-one)]piperidin-4-yl}-5H,11H-pyrrolo[2,1-c][1,4]benzoxazepine oxalate To 125 ml DMF were added 11-(piperidin-4-yl)-5H,11H-pyrrolo[2,1-c][1,4]benzoxazepine (10.0 g, 0.037 mole), beta-dimethylaminopropiophenone methiodide (12.7 g, 0.04 mole) and milled $K_2CO_3$ (10.0 g, 0.07 mole).

After stirring at ambient temperature for twenty hours, the mixture was poured into one liter water, stirred for five minutes and extracted with ether/ethyl acetate. The organic layer was washed twice with water and dried (saturated NaCl, anhydrous $MgSO_4$).

After filtering, the solvents were evaporated to 12.5 g (84%) of an oil, 4.0 g of which was dissolved in ether and acidified to pH 1 with ethereal oxalic acid. The resultant precipitate was collected and recrystallized three times from isopropanol/ether (1:10) to give a solid, d @ 132° C.

ANALYSIS: Calculated for $C_{26}H_{28}N_2O_2 \cdot (CO_2H)_2$: 68.55%C; 6.16%H; 5.71%N; Found: 68.01%C; 6.12%H; 5.51%N.

EXAMPLE 35

11-{1-[(3-Cyclohexyl-3-hydroxy-3-phenylpropyl)-]piperidin-4-yl}-5H,11H-pyrrolo[2,1-c][1,4]benzoxazepine maleate To a cold solution of cyclohexyl magnesium chloride (2.3M in ether, 10 ml, 0.023 mole) was added dropwise with stirring a solution of 11-{1-[3-(1-phenylpropan-1-one)]piperidin-4-yl}-5H,11H-pyrrolo[2,1-c][1,4]benzoxazepine (7.4 g, 0.018 mole) in 100 ml ether in about fifteen minutes.

After stirring at ambient temperature for one hour, the mixture was poured into 200 ml iced $NH_4Cl$ solution, stirred for five minutes, and then diluted with 200 ml ether. The ether layer was collected, washed twice with water and once with saturated NaCl, and dried over anhydrous $MgSO_4$.

After filtering, the solvent was evaporated to 8 g of a solid, which was purified via HPLC using 2% methanol/dichloromethane as an eluting solvent. The desired fractions were obtained, evaporated and dried to 4.0 g (44%) of a solid. This material was dissolved in ether and acidified to pH 1 with maleic acid. The resultant precipitate was collected and dried to afford 4.0 g (37%), m.p. 80° C. This material was recrystallized from isopropanol/ether (1:10) to yield a solid, m.p. 125° C. dec.

ANALYSIS: Calculated for $C_{32}H_{40}N_2O_2 \cdot C_4H_4O_4$: 71.97%C; 7.38%H; 4.66%N; Found: 71.61%C; 7.28%H; 4.40%N.

EXAMPLE 36

11-{1-[2-(4-Nitrophenylethyl)]piperidin-4-yl}-5H,11H-pyrrolo[2,1-c][1,4]benzoxazepine To a solution of 11-(piperidin-4-yl)-5H,11H-pyrrolo[2,1-c][1,4]benzoxazepine (4.4 g, 0.016 mole in 100 ml DMF), 10 g milled $K_2CO_3$ and 0.1 g KI was added 4-nitrophenethylbromide (4.53 g, 0.02 mole). This was heated at 60° C. for 4 hours.

The reaction was then quenched into water and extracted twice with ethyl acetate. The combined organics were washed with water and dried (saturated NaCl solution, anhydrous $MgSO_4$). This was filtered and concentrated to yield an oil.

The amine was purified via HPLC (1% methanol/dichloromethane) to yield 3.7 g (55%) of a solid, m.p. 141°–145° C.

This was recrystallized from isopropyl ether to yield an analytically pure solid, m.p. slight melt at 123°–125° C.; 144°–146° C.

ANALYSIS: Calculated for $C_{25}H_{27}N_3O_3$: 71.92%C; 6.52%H; 10.06%N; Found: 71.92%C; 6.59%H; 9.93%N.

EXAMPLE 37

11-{1-[2-(4-Benzyloxyphenyl)ethyl]piperidin-4-yl}-5H,11H-pyrrolo[2,1-c][1,4]benzoxazepine To a cold solution of 11-(piperidin-4-yl)-5H,11H-pyrrolo[2,1-c][1,4]benzoxazepine (6.0 g, 0.022 mole) and triethylamine (3.6 ml, 0.025 mole) in 25 ml dichloromethane was added a solution of 4-benzyloxyphenacetyl chloride (6.5 g, 0.025 mole) in 50 ml dichloromethane (DCM, hereinafter). The addition took ten minutes and stirring was continued for five hours at ambient temperature.

The DCM solution was washed with 100 ml water and dried over anhydrous $Na_2SO_4$.

After filtering, the solvent was evaporated to 13 g of an oil, which was purified via HPLC on a silica gel column using 5% ethyl acetate in DCM as an eluting solvent.

The desired fractions were collected and evaporated to a clear glass to yield 9.0 g (83%) of the desired amide.

To a cold solution of $LiAlH_4$ (1M in THF, 30 ml, 0.03 mole), was added a solution of the amide (9.0 g, 0.018 mole) in 60 ml THF in about fifteen minutes. After stirring at ambient temperature for one hour, the mixture was cooled, quenched with 20 ml saturated $NH_4Cl$ solution and filtered. The filtrate was diluted with 200 ml ethyl acetate, washed twice with water and dried (saturated NaCl, anhydrous $MgSO_4$).

After filtering, the solvents were evaporated to 7.0 g of a solid, m.p. 129°–133° C. This material was purified via HPLC on a silica gel column using ethyl acetate/DCM/diethylamine (20:80:1). The desired fraction was concentrated to 6.0 g (66%) of a solid, m.p. 126°–127° C. This material was recrystallized from isopropyl ether to give needles, m.p. 127°–128° C.

ANALYSIS: Calculated for $C_{32}H_{34}N_2O_2$: 80.30%C; 7.16%H; 5.85%N; Found: 80.07%C; 7.05%H; 5.86%N.

EXAMPLE 38

11-{1-[2-(4-Hydroxyphenyl)ethyl]piperidin-4-yl}-5H,11H-pyrrolo[2,1-c][1,4]benzoxazepine To 200 ml isopropanol was added 11-{1-[2-(4-benzyloxyphenyl)ethyl]piperidin-4-yl}-5H,11H-pyrrolo[2,1-c][1,4]benzoxazepine (2.8 g, 0.006 mole) and 10% Pd/C (3.0 g). After shaking on a Parr apparatus under 50 psi of hydrogen for twenty-four hours, the solution was filtered and evaporated to a solid (2.2 g, m.p. 77° C.).

This material was dissolved in ethyl acetate, eluted through a silica gel column with ethyl acetate and concentrated to 2.0 g (83%) of a solid, m.p. 87°–89° C.

ANALYSIS: Calculated for $C_{25}H_{28}N_2O_2$: 77.29%C; 7.26%H; 7.21%N; Found: 77.24%C; 7.40%H; 7.07%N.

EXAMPLE 39

11-{1-[2-(3,4-Dichlorophenylethyl)]piperidin-4-yl}-5H,11H-pyrrolo[2,1-c][1,4]benzoxazepine To a cold solution of 11-(piperidin-4-yl)-5H,11H-pyrrolo[2,1-c][1,4]benzoxazepine (4.20 g, 0.016 mole in 80 ml DCM) and 2.4 ml (0.017 mole) triethylamine was added a solution of 3,4-dichlorophenacetyl chloride (3.85 g, 0.017 mole in 20 ml DCM). This was stirred for 15 minutes at ice bath temperature.

The reaction mixture was diluted with additional dichloromethane, washed with water and dried (saturated NaCl solution, anhydrous $Na_2SO_4$).

The amide was purified via flash chromatography ($Et_2O$) to yield 5.85 g (81%) of a solid, m.p. 71°–75° C.

A cooled solution of 11-[1-(3,4-dichlorophenacetyl)-piperidin-4-yl]-5H,11H-pyrrolo[2,1-c][1,4]benzoxazepine (5.1 g, 0.011 mole in 80 ml THF) was added to 17 ml of one molar solution of lithium aluminum hydride in THF. This was stirred at ice bath temperature for fifteen minutes.

The reaction was quenched to a precipitate with a saturated $NH_4Cl$ solution, filtered and diluted with ethyl acetate, washed twice with a dilute NaCl solution and dried (saturated NaCl solution, anhydrous $MgSO_4$). This was filtered and concentrated to an oil.

The amine was purified via HPLC (EtOAc/hexane) to yield 2.2 g (37%) of a solid, m.p. 88°–99° C. This was recrystallized from isopropyl ether to yield an analytically pure solid, m.p. 110°–113.5° C.

ANALYSIS: Calculated for $C_{25}H_{26}Cl_2N_2O$: 68.03%C; 5.94%H; 6.35%N; Found: 68.08%C; 5.98%H; 6.30%N.

EXAMPLE 40

11-{1-[2-(3,4-Dimethoxyphenyl)ethyl]piperidin-4-yl}-5H,11H-pyrrolo[2,1-c][1,4]benzoxazepine To a cold solution of 11-(piperidin-4-yl)-5H,11H-pyrrolo[2,1-c][1,4]benzoxazepine (4.0 g, 0.015 mole) and triethylamine (2.9 ml, 0.02 mole) in 25 ml DCM was added a solution of 3,4-dimethoxyphenacetyl chloride (4.3 g, 0.02 mole) in 25 ml DCM.

After stirring at ambient temperature for three hours, the solution was washed with 100 ml water, dried over anhydrous $MgSO_4$, filtered and evaporated to about 9 g of a semi-solid, which was eluted on a silica gel column with ethyl acetate/DCM (1:4) via HPLC to yield 5.0 g (75%) of a clear glass.

To a cold solution of $LiAlH_4$ (1M THF solution, 20 ml, 0.02 mole) was added a solution of the above amide in 50 ml THF. After stirring at ambient temperature for one hour, the mixture was cooled, quenched with 20 ml saturated $NH_4Cl$ solution, diluted with 200 ml ethyl acetate and filtered. The filtrate was washed with water and dried (saturated NaCl, anhydrous $MgSO_4$).

After filtering, the solvents were evaporated to 4.5 g of a semi-solid, which was eluted on a silica gel column with ethyl acetate via HPLC to yield 3.4 g (77%) of a solid, m.p. 114° C. This material was recrystallized twice from isopropyl ether to yield a solid, m.p. 119°–120° C.

ANALYSIS: Calculated for $C_{27}H_{32}N_2O_3$: 74.97%C; 7.46%H; 6.48%N; Found: 74.54%C; 7.39%H; 6.18%N.

EXAMPLE 41

11-{1-[2-(4-Dimethylaminophenylethyl)]piperidin-4-yl}-5H,11H-pyrrolo[2,1-c][1,4]benzoxazepine To a solution of 11-(piperidin-4-yl)-5H,11H-pyrrolo[2,1-c][1,4]benzoxazepine (3.53 g, 0.013 moles), 10 g $K_2CO_3$ and 0.1 g KI in 100 ml DMF was added a solution of 4-dimethylaminophenethyl chloride (2.85 g; 0.015 mole in 15 ml DMF). This was heated at 75° C. for 10 hours.

The reaction was quenched into iced water and extracted three times with ethyl acetate. The combined organics were washed with water and dried (saturated NaCl solution, anhydrous $MgSO_4$). This solution was filtered and concentrated to give an oil.

The amine was purified via HPLC (3% MeOH/DCM) to yield 1.8 g (33%) of a solid, m.p. 94°–99° C. This was recrystallized from isopropyl ether to give an analytically pure solid, m.p. 98°–99.5° C.

ANALYSIS: Calculated for $C_{27}H_{33}N_3O$: 78.04%C; 8.00%H; 10.11%N; Found: 77.89%C; 8.07%H; 10.05%N.

EXAMPLE 42

11-{1-[2-(2-Methoxyphenyl)ethyl]piperidin-4-yl}-5H,11H-pyrrolo[2,1-c][1,4]benzoxazepine To a cooled solution of 11-(piperidin-4-yl)-5H,11H-pyrrolo[2,1-c][1,4]benzoxazepine (6.2 g, 0.023 mole in 80 ml DCM) and triethylamine (3.5 ml, 0.025 mole) was slowly added a solution (in DCM) of 2-methoxyphenacetyl chloride (4.62 g, 0.025 mole). This was stirred at room temperature for 30 minutes.

The reaction was diluted with additional dichloromethane, washed twice with water and dried (saturated NaCl solution, anhydrous $Na_2SO_4$). This was filtered and concentrated to yield an oil.

The amide was purified via flash chromatography (5% EtOAc/DCM) to yield 8.5 g (89%) of a solid, m.p. 72°–76° C.

A solution of 11-[1-(2-methoxyphenacetyl)piperidin-4-yl]-5H,11H-pyrrolo[2,1-c][1,4]benzoxazepine (8.15 g, 0.019 mole in 120 ml THF) was added to a cooled solution of lithium aluminum hydride in THF (40 ml, 0.04 mole diluted to 140 ml total volume with THF). This was stirred at room temperature for 45 minutes.

The reaction was quenched with a saturated $NH_4Cl$ solution, filtered and diluted with ethyl acetate. The combined organics were washed three times with a dilute NaCl solution and dried (saturated NaCl solution, anhydrous $Na_2SO_4$).

The amine was purified via flash chromatography (5% MeOH/DCM) to yield 5.8 g (73% from the secondary amine) of a solid, m.p. 119°–125° C. This was recrystallized from isopropyl ether to give an analytically pure solid, m.p. 126°–128.5° C.

ANALYSIS: Calculated for $C_{26}H_{30}N_2O_2$: 77.58%C; 7.51%H; 6.96%N; Found: 77.48%C; 7.54%H; 6.92%N.

EXAMPLE 43

11-[(1-Butyl)piperidin-4-yl]-5H,11H-pyrrolo[2,1-c][1,4]benzoxazepine

A solution of 11-piperidin-4-yl)-5H,11H-pyrrolo[2,1-c][1,4]benzoxazepine (6.1 g, 0.023 mole), 1-chlorobutane (2.42 g, 0.026 mole), $K_2CO_3$ (10 g) and KI (0.1 g) in 100 ml dimethylformamide was heated at 70° C. for a total of 7 hours.

The reaction was quenched into water and extracted three times with ethyl acetate. The combined organics were washed with water and dried (saturated NaCl solution, anhydrous MgSO$_4$). This was filtered and concentrated to give an oil.

The amine was purified via HPLC (4% MeOH/DCM) to yield 3.6 g (48%) of a solid, m.p. 82°–94° C. This was recrystallized from diethyl ether/hexane (1:1) to give an analytically pure solid, m.p. 84.5°–87° C.

ANALYSIS: Calculated for C$_{21}$H$_{28}$N$_2$O: 77.74%C; 8.70%H; 8.63%N; Found: 77.98%C; 8.94%H; 8.67%N.

EXAMPLE 44

11-{1-[2-(3-Methoxyphenyl)ethyl]piperidin-4-yl}-5H,11H-pyrrolo[2,1-c][1,4]benzoxazepine fumarate To a cooled solution of 11-(piperidin-4-yl)-5H,11H-pyrrolo[2,1-c][1,4]benzoxazepine (6.7 g, 0.025 mole) and triethylamine (4.2 ml, 0.03 mole) in 100 ml dichloromethane was added 3-methoxyphenacetyl chloride (5.0 g, 0.027 mole in 15 ml DCM). This was stirred for 15 minutes at ice bath temperature.

The mixture was diluted with additional dichloromethane, washed twice with water and dried (saturated NaCl solution, anhydrous Na$_2$SO$_4$). The solution was then concentrated to an oil.

The amide was purified via flash chromotography (10% EtOAc/DCM) to yield 8.3 g (80%) of a solid, m.p. 136°–140° C.

A solution of 11-[1-(3-methoxyphenacetyl)piperidin-4-yl]-5H,11H-pyrrolo[2,1-c][1,4]benzoxazepine (8.2 g, 0.02 mole) in 110 ml tetrahydrofuran was added to a cooled 1 molar solution of lithium aluminum hydride in tetrahydrofuran (40 ml, 0.04 mole diluted with 80 ml THF). This was stirred at ambient temperature for one hour.

The reaction was then quenched to a precipitate with a saturated NH$_4$Cl solution. This was filtered and washed with ethyl acetate. The combined organics were washed twice with a dilute NaCl solution and dried (saturated NaCl solution, anhydrous MgSO$_4$). This was filtered and concentrated to an oil.

The amine was purified via HPLC (EtOAc/DCM) to yield 6.0 g (60%) from the starting amine) of an oil.

A portion of this amine was made into the fumarate salt by addition of an ethereal solution of fumaric acid to give a solid, m.p. 100°–130° C. This was recrystallized three times from isopropanol/diethyl ether (1:2) to give an analytically pure solid, m.p. 143°–145° C.

ANALYSIS: Calculated for C$_{26}$H$_{30}$N$_2$O$_2$·C$_4$H$_4$O$_4$: 69.48%C; 6.61%H; 5.40%N; Found: 69.08%C; 6.66%H; 5.30%N.

EXAMPLE 45

11-{1-[2-(2,3-Dimethoxyphenyl)ethyl]piperidin-4-yl}-5H,11H-pyrrolo[2,1-c][1,4]benzoxazepine fumarate A mixture of 11-(piperidin-4-yl)-5H,11H-pyrrolo[2,1-c][1,4]benzoxazepine (2.93 g, 0.011 mole), K$_2$CO$_3$ (10 g), KI (0.1 g) and 2,3-dimethoxyphenethyl chloride (2.45 g, 0.012 mole) in 100 ml of n-butyl acetate was heated at reflux for 50 hours. The mixture was then filtered and concentrated to give 5.5 g of an oil.

The amine was purified via HPLC (EtOAc/DCM/MeOH; 50:50:1) to yield 2.7 g (57%) of an oil. The fumarate salt was then formed by addition of etheral fumaric acid to give 2.6 g of a solid, m.p. 120°–146° C. This was recrystallized twice from ethyl acetate/methanol (10:1) to give an analytically pure solid, m.p. 150°–152° C.

ANALYSIS: Calculated for C$_{27}$H$_{32}$N$_2$O$_3$·C$_4$H$_4$O$_4$: 67.87%C; 6.61%H; 5.11%N; Found: 67.55%C; 6.63%H; 5.08%N.

EXAMPLE 46

11-{1-[2-(3-Trifluoromethylphenyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (6.15 g, 0.023 mole), 2-(3-trifluoromethylphenyl)ethyl menthanesulfonate (7.27 g, 0.027 mole) and K$_2$CO$_3$ (10.6 g) in 125 ml dimethylformamide was heated at 65° C. for 5 hours.

The reaction was quenched into iced water and extracted twice with ethyl acetate. The combined organics were washed twice with water and dried (saturated NaCl solution, anhydrous MgSO$_4$). This was then concentrated to an oil.

The amine was purified via HPLC (EtOAc (EtOAc/DCM/Et$_2$NH; 5:95:0.5) to yield 4.75 g (47%) of a solid, m.p. 92°–99° C. This was recrystallized from isopropyl ether to give an analytically pure solid, m.p. 99°–100.5° C.

ANALYSIS: Calculated for C$_{26}$H$_{27}$F$_3$N$_2$O: 70.89%C; 6.18%H; 6.36%N; Found: 70.93%C; 6.20%H; 6.32%N.

EXAMPLE 47

11-{1-[2-(3-Chlorophenyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (6.05 g, 0.023 mole), 3-chlorophenethyl chloride (4.74 g, 0.027 mole), K$_2$CO$_3$ (10.9 g) and KI (0.1 g) in 130 ml n-butyl acetate was refluxed for 50 hours. The reaction mixture was cooled, filtered and concentrated to an oil.

The amine was purified via HPLC (1% MeOH/CH$_2$Cl$_2$) to give 4.15 g (44%) of a solid, m.p. 101°–107° C. This was recrystallized from isopropyl ether to give an analytically pure solid, m.p. 98°–100° C.

ANALYSIS: Calculated for C$_{25}$H$_{27}$ClN$_2$O: 73.79%C; 6.69%H; 6.88%N; Found: 73.86%C; 6.86%H; 6.88%N.

EXAMPLE 48

11-{1-[2-(3,4,5-Trimethoxyphenyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (5.8 g, 0.022 mole), K$_2$CO$_3$ (11.0 g) and 2-(3,4,5-trimethoxyphenyl)ethyl methanesulfonate (7.53 g, 0.026 mole) in 120 ml dimethylformamide was heated at 70° C. for 4.5 hours.

The reaction was quenched into iced water and extracted twice with ethyl acetate. The organics were washed with water and dried (saturated NaCl solution, anhydrous Na$_2$SO$_4$). This was concentrated to an oil.

The amine was purified via HPLC (EtOAc/DCM) to yield 5.9 g (58%) of a solid, m.p. 91°–99° C. This was recrystallized twice from isopropyl ether to give an analytically pure solid, m.p. 86°–88° C.

ANALYSIS: Calculated for C$_{24}$H$_{34}$N$_2$O$_4$: 72.70%C; 7.41%H; 6.06%N; Found: 72.58%C; 7.35%H; 5.95%N.

EXAMPLE 49

11-{1-[2-(4-Hydroxy-3-methoxyphenyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (5.1 g, 0.019 mole), 4-hydroxy-3-methoxyphenethyl chloride (4.25 g, 0.023 mole) and NaHCO$_3$ (11 g) in 110 ml n-butyl acetate was heated at reflux for 18 hours. The reaction mixture was then cooled, filtered and concentrated to an oil.

The amine was purified via HPLC (EtOAc/DCM/MeOH; 25:75:1) to yield 5.65 g (71%) of a solid, m.p. d @ 163°-172° C. A portion of this solid was recrystallized from isopropyl ether/methanol (10:1) to give an analytically pure solid, m.p. d @ 169.5°-172° C.

ANALYSIS: Calculated for C$_{26}$H$_{30}$N$_2$O$_3$: 74.61%C; 7.22%H; 6.69%N; Found: 74.23%C; 7.24%H; 6.51%N.

EXAMPLE 50

8-Chloro-11-[(1-methyl)piperidin-4-yl]-5H,11H-pyrrolo[2,1-c][1,4]benzoxazepine

A mixture of [1-(4-chloro-2-fluorobenzyl)-2-pyrryl][(1-methyl)piperidin-4-yl]methanol (0.65 g, 0.002 mole) and sodium hydride (50% in oil, 0.12 g, 0.0023 mole, washed once with hexane) in 25 ml 20% DMF/benzene was heated at 80° C. for seven hours.

The reaction was quenched into an iced NaCl solution and stirred with ethyl acetate. The layers were separated and the aqueous layer was extracted with ethyl acetate. The combined organics were washed with water and dried (saturated NaCl solution, anhydrous Na$_2$SO$_4$). This was filtered and concentrated to yield 0.63 g of a solid, m.p. 155°-171° C. This was recrystallized from isopropyl ether to give 0.35 g (55%) of a solid, m.p. 177°-179.5° C.

ANALYSIS: Calculated for C$_{18}$H$_{21}$ClN$_2$O: 68.24%C; 6.68%N; 8.84%N; Found: 68.02%C; 6.80%H; 8.70%N.

EXAMPLE 51

11-{1-[2-(2-Thienyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (4.65 g, 0.017 mole), 2-thiophenethylmethanesulfonate (4.13 g, 0.02 mole) and K$_2$CO$_3$ (10 g) in 135 ml dimethylformamide was heated at 70° C. for 4 hours.

The reaction was quenched into water and extracted twice with ethyl acetate. The organics were washed with water and dried (saturated NaCl solution, anhydrous Na$_2$SO$_4$). This was then concentrated to an oil.

The amide was purified via HPLC (DCM/EtOAc/MeOH; 75:25:1) to yield 3.9 g (61%) of a solid, m.p. 77°-85° C. A 3.6 g portion of this was recrystallized from isopropyl ether/petroleum ether (1:2) to yield 2.25 g (38%) of an analytically pure solid, m.p. 83°-85° C.

ANALYSIS: Calculated for C$_{23}$H$_{26}$N$_2$OS: 72.98%C; 6.92%H; 7.40%N; Found: 73.25%C; 7.19%H; 7.38%N.

EXAMPLE 52

11-{1-[3-(4-Chlorophenyl)propan-3-one)piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (5.1 g, 0.019 mole), beta,para-dichloropropiophenone (4.47 g, 0.022 mole), K$_2$CO$_3$ (10.5 g) and 130 ml n-butyl acetate was heated at 130° C. for 15 minutes. This was then cooled, filtered and concentrated to an oil.

The amine was purified via HPLC (ethyl acetate/dichloromethane/methanol, 20:8:1) to yield 2.7 g (33%) of a solid, m.p. 123°-126° C. This was recrystallized from isopropyl ether to give 2.35 g (28%) of an analytically pure solid, m.p. 124°-127° C.

ANALYSIS: Calculated for C$_{26}$H$_{27}$ClN$_2$O$_2$: 71.80%C; 6.26%H; 6.44%N; Found: 71.74%C; 6.51%H; 6.30%N.

EXAMPLE 53

11-{1-[2-(4-Trifluoromethylphenyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (5.07 g, 0.019 mole), (p-trifluoromethylphenyl)ethyl methanesulfonate (6.08 g, 0.023 mole) and K$_2$CO$_3$ (10.7 g) in 150 ml dimethylformamide was heated at 90° C. for 7 hours.

The reaction was then quenched into iced water and extracted twice with ethyl acetate. The organics were washed with water and dried (saturated NaCl solution, anhydrous MgSO$_4$).

The amine was purified via HPLC (ethyl acetate/dichloromethane/methanol, 10:90:1) to yield 3.75 g (45%) of a solid, m.p. 80°-85° C. This was recrystallized from isopropyl ether/hexane (1:3) to give 2.3 g (27%) of an analytically pure solid, m.p. 85°-88° C.

ANALYSIS: Calculated for C$_{26}$H$_{27}$F$_3$N$_2$O: 70.89%C; 6.18%H; 6.36%N; Found: 71.15%C; 6.17%H; 6.44%N.

EXAMPLE 54

11-{1-[2-(2-Fluorophenyl)ethyl]piperidin-4-yl}-5H,11H-pyrrolo[2,1-c][1,4]benzoxazepine A mixture of 11-(piperidin-4-yl)-5H,11H-pyrrolo[2,1-c][1,4]benzoxazepine (5.0 g, 0.019 mole), (2-fluorophenyl)ethyl methanesulfonate (4.47 g, 0.02 mole), K$_2$CO$_3$ (11 g) and 150 ml dimethylformamide was heated at 85° C. for 9 hours.

The reaction was then quenched into iced water and extracted twice with ethyl acetate. The organics were washed with water and dried (saturated NaCl solution, anhydrous MgSO$_4$). This was filtered and concentrated to an oil.

The amine was purified via HPLC (2% MeOH/DCM) to yield 3.9 g (54%) of a solid, m.p. 80°-91° C. This was recrystallized from isopropyl ether/hexane (1:2) to yield 2.19 g (30%) of a solid, m.p. 96°-99° C.

ANALYSIS: Calculated for C$_{25}$H$_{27}$FN$_2$O: 76.89%C; 6.97%H; 7.17%N; Found: 76.81%C; 7.01%H; 7.19%N.

EXAMPLE 55

11-{1-[3-(4-Fluorophenyl)propan-3-one]piperidin-4-yl}-5H,11H-pyrrolo[2,1-c][1,4]benzxazepine A mixture of 11-(piperidin-4-yl)-5H,11H-pyrrolo[2,1-c][1,4]benzoxazepine (5.2 g, 0.019 mole), beta-chloro-4-fluoropropiophenone (4.16 g, 0.022 mole) and K$_2$CO$_3$ (10.7 g) in 130 ml n-butyl acetate was heated at 130° C. for 20 minutes. The mixture was then filtered and concentrated to an oil.

The amine was purified via HPLC (1% MeOH/DCM) to yield 3.15 g (40%) of a solid, m.p. 111°-116° C. This was recrystallized from isopropyl ether/hexane (1:1) to yield 2.02 g (25%) of an analytically pure solid, m.p. 104°-109° C.

ANALYSIS: Calculated for $C_{26}H_{27}FN_2O_2$: 74.62%C; 6.50%H; 6.69%N; Found: 74.81%C; 6.63%H; 6.71%N.

EXAMPLE 56

11-{1-[4-(4-Fluorophenyl)butan-4-ol]piperidin-4-yl}-5H,11H-pyrrolo[2,1-c][1,4]benzoxazepine fumarate A mixture of 11-(piperidin-4-yl)-5H,11H-pyrrolo[2,1-c][1,4]benzoxazepine (5.1 g, 0.019 mole), 4-chloro-1-(4-fluorophenyl)butanol (4.62 g, 0.022 mole), $K_2CO_3$ (10.2 g) and KI (0.1 g) in 130 ml n-butylacetate was heated at 145° C. for 48 hours. The reaction was then cooled, filtered and concentrated to an oil.

The amine was purified via HPLC (3% MeOH/DCM) to yield 2.3 g (28%) of a solid, m.p. 57°-67° C. The fumarate salt of the amine was formed by the addition of a fumaric acid/diethyl ether solution to give 1.85 g (18%) of an analytically pure solid, m.p. 95°-105° C.

ANALYSIS: Calculated for $C_{27}H_{31}FN_2O_2 \cdot C_4H_4O_4$: 67.62%C; 6.41%H; 5.09%N; Found: 67.24%C; 6.37%H; 5.14%N.

EXAMPLE 57

7-Chloro-11-[(1-methyl)piperidin-4-yl]-5H,11H-pyrrolo[2,1-c][1,4]benzoxazepine

To a suspension of sodium hydride (60% in oil, washed once with hexane) in 75 ml of 25% DMF/benzene mixture was added a solution of [1-(5-chloro-2-fluorobenzyl)-2-pyrryl]-[(1-methyl)piperidin-4-yl]methanol (83.7 g, 0.248 mole in 200 ml 25% DMF/benzene). This was heated at 70° C. for 3.5 hours.

The reaction was then quenched with water. The aqueous phase was extracted twice with ethyl acetate and dried (saturated NaCl solution, anhydrous $Na_2SO_4$). This solution was filtered and concentrated to yield 59.2 g (75%) of a solid, m.p. 165°-167.5° C.

A 5.0 g portion of the solid was recrystallized from tetrahydrofuran/diethyl ether (2:3) to yield 3.05 g of analytically pure solid, m.p. 165°-167.5° C.

ANALYSIS: Calculated for $C_{18}H_{21}ClN_2O$: 68.24%C; 6.68%H; 8.84%N; Found: 68.54%C; 6.79%H; 9.04%N.

EXAMPLE 58

N-Phenyl-4-(5H,11H-pyrrolo[2,1-c][1,4]benzoxazepine-11-yl)-1-piperidine carboxamide A solution of 11-(piperdin-4-yl)-5H,11H-pyrrolo[2,1-c][1,4]benzoxazepine (4.8 g, 0.018 mole) and phenylisocyanate (2.14 ml, 0.02 mole) in 140 ml benzene was heated at 65° C. for 1 hour. The reaction mixture was then cooled. The product was filtered and dried to yield 6.25 g (90%) of a solid, m.p. 184°-192° C. This was recrystallized from tetrahydrofuran/diethyl ether (1:4) to yield 5.9 g (85%) of an analytically pure solid, m.p. 167°-170° C.

ANALYSIS: Calculated for $C_{24}H_{25}N_3O_2$: 74.39%C; 6.50%H; 10.84%N; Found: 74.38%C; 6.61%H; 10.88%N.

EXAMPLE 59

7-Chloro-11-(piperidin-4-yl)-5H,11H-pyrrolo[2,1-c][1,4]benzoxazepine

To a mixture of 7-chloro-11-[(1-methyl)piperidin-4-yl]-5H,11H-pyrrolo[2,1-c][1,4]benzoxazepine (11.95 g, 0.038 mole) and $K_2CO_3$ (22 g) in 200 ml dichloromethane was added 2,2,2-trichloroethylchloroformate (8.8 g, 0.04 mole). This was stirred at ambient temperature for 30 hours.

The mixture was then added to water and extracted twice with dichloromethane. The combined organics were washed with a saturated $NaHCO_3$ solution and water, and dried (saturated NaCl solution, anhydrous $Na_2SO_4$). This was filtered and concentrated to an oil.

The carbamate was purified via flash chromatography to yield 14.6 g (80%) of an oil. This was used without further purification.

To a solution of the carbamate intermediate (14.5 g in 150 ml THF) was added at ice bath temperature, glacial acetic acid (3.6 g, 0.06 mole) and activated zinc metal (washed once with dilute HCl and twice with $H_2O$). The mixture was stirred at ambient temperature for ½ hour, filtered and concentrated. The resulting oil was taken up in a saturated $Na_2CO_3$ solution and extracted twice with ethyl acetate. The combined organics were washed with water and dried (saturated NaCl solution, anhydrous $MgSO_4$). This was filtered and concentrated to an oil.

The amine was purified via HPLC (tetrahydrofuran/diethyl amine, 100:1) to yield 5.6 g (62%, 49% from N-methyl amine) of a solid, m.p. 98°-110° C. A portion of this was recrystallized from isopropyl ether/hexane (1:1) to give an analytically pure solid, m.p. 115°-117° C.

ANALYSIS: Calculated for $C_{17}H_{19}ClN_2O$: 67.43%C; 6.32%H; X.XX%N; Found: 67.68%C; 6.44%H; Y.YY%N.

EXAMPLE 60

11-{1-[2-(2-Trifluoromethylphenyl)ethyl]piperidin-4-yl}-5H,11H-pyrrolo[2,1-c][1,4]benzoxazepine fumarate A mixture of 11-(piperidin-4-yl)-5H,11H-pyrrolo[2,1-c][1,4]benzoxazepin (4.93 g, 0.018 mole), 2-(2-trifluoromethylphenyl)ethyl methanesulfonate (5.41 g, 0.021 mole) and $K_2CO_3$ (10.8 g) in 150 ml dimethylformamide was heated at 75° C. for 4½ hours.

The reaction was then quenched into water and extracted twice with ethyl acetate. The combined organics were washed with water and dried (saturated NaCl solution, anhydrous $MgSO_4$). This was filtered and concentrated to an oil.

The amine was purified via HPLC (30% EtOAc/DCM) to yield 2.65 g (33%) of an oil. The fumarate salt was formed by adding 1 equivalent of fumaric acid in isopropanol to a solution of the amine in isopropanol. The fumarate which crystallized was filtered and triturated in boiling methanol/isopropanol to yield 2.35 g (23%) of a solid, m.p. d @ 186°-188° C.

ANALYSIS: Calculated for $C_{26}H_{27}F_3N_2O \cdot C_4H_4O_4$: 64.74%C; 5.61%H; 5.03%N; Found: 64.90%C; 5.76%H; 4.94%N.

EXAMPLE 61

3-Methyl-11-[(1-methyl)piperidin-4-yl]-5H,11H-pyrrolo[2,1-c][1,4]benzoxazepine

To a suspension of sodium hydride (3.20 g, 60% dispersion in oil, washed twice with hexane) in 20 ml dimethylformamide/benzene (20:80) was added a solution of [1-(2-fluorobenzyl)-5-methylpyrrol-2-yl][(1-methyl)-piperidin-4-yl]methanol (15.45 g, 0.088 mole) in 80 ml of the same solvent. This was heated at 70° C. for 5 hours.

The reaction was then quenched into iced water and extracted twice with ethyl acetate. The combined organics were washed twice with water and dried (saturated NaCl solution, anhydrous Na₂SO₄). This was concentrated to a semi-solid.

The amine was purified via HPLC (4% MeOH/DCM) to yield 9.90 g (68%) of a solid, m.p. 131°–136° C. This was recrystallized twice from isopropyl ether/hexane (1:2) to yield an analytically pure solid, m.p. 136°–138.5° C.

ANALYSIS: Calculated for $C_{19}H_{24}N_2O$: 76.99%C; 8.16%H; 9.45%N; Found: 77.07%C; 8.26%H; 9.40%N.

We claim:

1. A compound having the formula

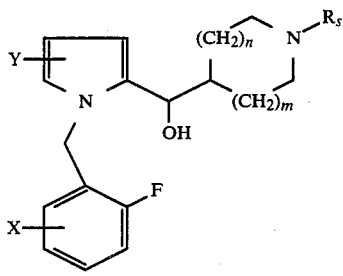

where m and n are each independently 0, 1 or 2 and m+n=1 or 2, X and Y are each independently hydrogen, loweralkyl or halogen, and $R_s$ is methyl or benzyl.

2. The compound as defined in claim 1, where m is 1 and n is 1.

3. The compound as defined in claim 2, where Y is methyl.

4. The compound as defined in claim 3, where X is hydrogen.

5. The compound as defined in claim 4, where $R_s$ is methyl which is [1-(2-fluorobenzyl)-5-methyl-2-pyrryl]-[(1-methyl)piperidin-4-yl]methanol.

6. The compound as defined in claim 2, where Y is hydrogen.

7. The compound as defined in claim 6, wherein X is chlorine.

8. The compound as defined in claim 7, where $R_s$ is methyl which is [1-(4-chloro-2-fluorobenzyl)-2-pyrryl]-[(1-methyl)piperidin-4-yl]methanol.

9. The compound as defined in claim 7, where $R_s$ is methyl which is [1-(5-chloro-2-fluorobenzyl)-2-pyrryl]-[(1-methyl)piperidin-4-yl]methanol.

10. The compound as defined in claim 6, where X is hydrogen and $R_s$ is methyl, which is [1-(2-fluorobenzyl)-2-pyrryl][(1-methyl)piperidin-4-yl]methanol.

* * * * *